United States Patent
McMillan et al.

(10) Patent No.: US 8,681,340 B2
(45) Date of Patent: Mar. 25, 2014

(54) MICROVOLUME ANALYSIS SYSTEM

(76) Inventors: Norman McMillan, County Carlow (IE); Stuart Smith, County Wicklow (IE); Martina O'Neill, Dublin (IE); Michael Baker, County Carlow (IE)

( * ) Notice: Subject to any disclaimer, the term of this patent is extended or adjusted under 35 U.S.C. 154(b) by 848 days.

(21) Appl. No.: 12/227,266

(22) PCT Filed: May 10, 2007

(86) PCT No.: PCT/EP2007/054546
§ 371 (c)(1),
(2), (4) Date: Jun. 29, 2010

(87) PCT Pub. No.: WO2007/131945
PCT Pub. Date: Nov. 22, 2007

(65) Prior Publication Data
US 2010/0277742 A1    Nov. 4, 2010

(30) Foreign Application Priority Data

May 12, 2006 (IE) .................................. S2006/0381
Mar. 23, 2007 (EP) ..................................... 07104842

(51) Int. Cl.
*G01B 11/02* (2006.01)
(52) U.S. Cl.
USPC ............................ 356/503; 356/451; 356/445
(58) Field of Classification Search
USPC ................................................ 356/450, 503
See application file for complete search history.

(56) References Cited

U.S. PATENT DOCUMENTS

| 4,910,402 | A  | * | 3/1990  | McMillan ................. 250/341.2 |
| 6,628,382 | B2 |   | 9/2003  | Robertson |
| 6,809,826 | B2 |   | 10/2004 | Robertson |
| 2007/0273883 | A1 | * | 11/2007 | Dickopf et al. ............... 356/445 |

OTHER PUBLICATIONS

McMillan et al (A fiber drop analyzer: A new analytical instrument for the individual, sequential, or collective measurement of the physical and chemical properties of liquids, Review of Scientific Instruments, vol. 63, No. 6, Jun. 1992, pp. 3431-3454, XP000301849 ISSN: 0034-6748).*
Song et al (Review of drop analysis technology for liquid property study, Opto-Electronics Review 13, No. 1, 2005).*

* cited by examiner

*Primary Examiner* — Tarifur Chowdhury
*Assistant Examiner* — Jonathon Cook
(74) *Attorney, Agent, or Firm* — Whiteford, Taylor & Preston, LLP; Gregory M. Stone

(57) ABSTRACT

An analyzer comprising a source of electromagnetic radiation, a detector for said radiation and a drophead comprising a surface which is adapted to receive a drop of liquid to be tested, the drophead being positioned in use relative to the source and detector to illuminate a drop received thereon and to cause an interaction in the path of the electromagnetic radiation between the source and detector, characterized in that said surface of said drophead is dimensioned to constrain the drop to adopt a shape which is dominated more by surface tension forces than by gravitational forces.

31 Claims, 17 Drawing Sheets

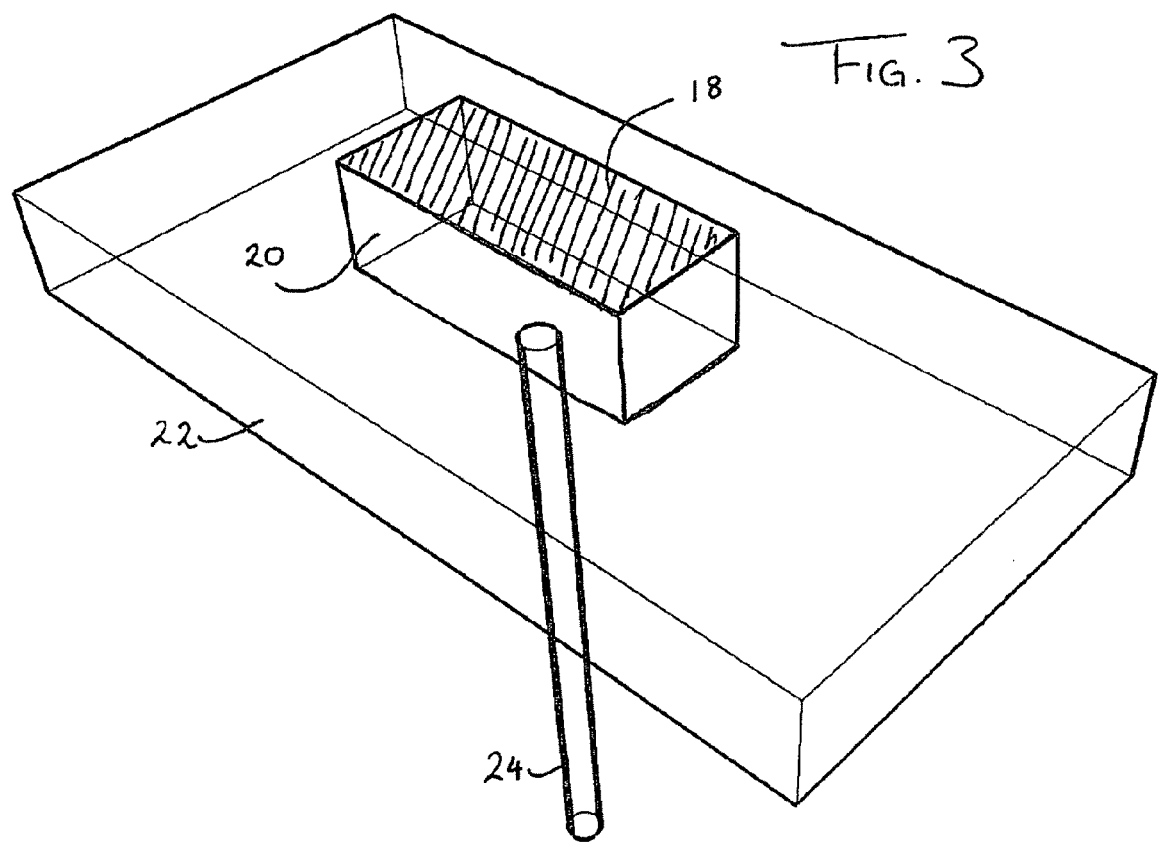

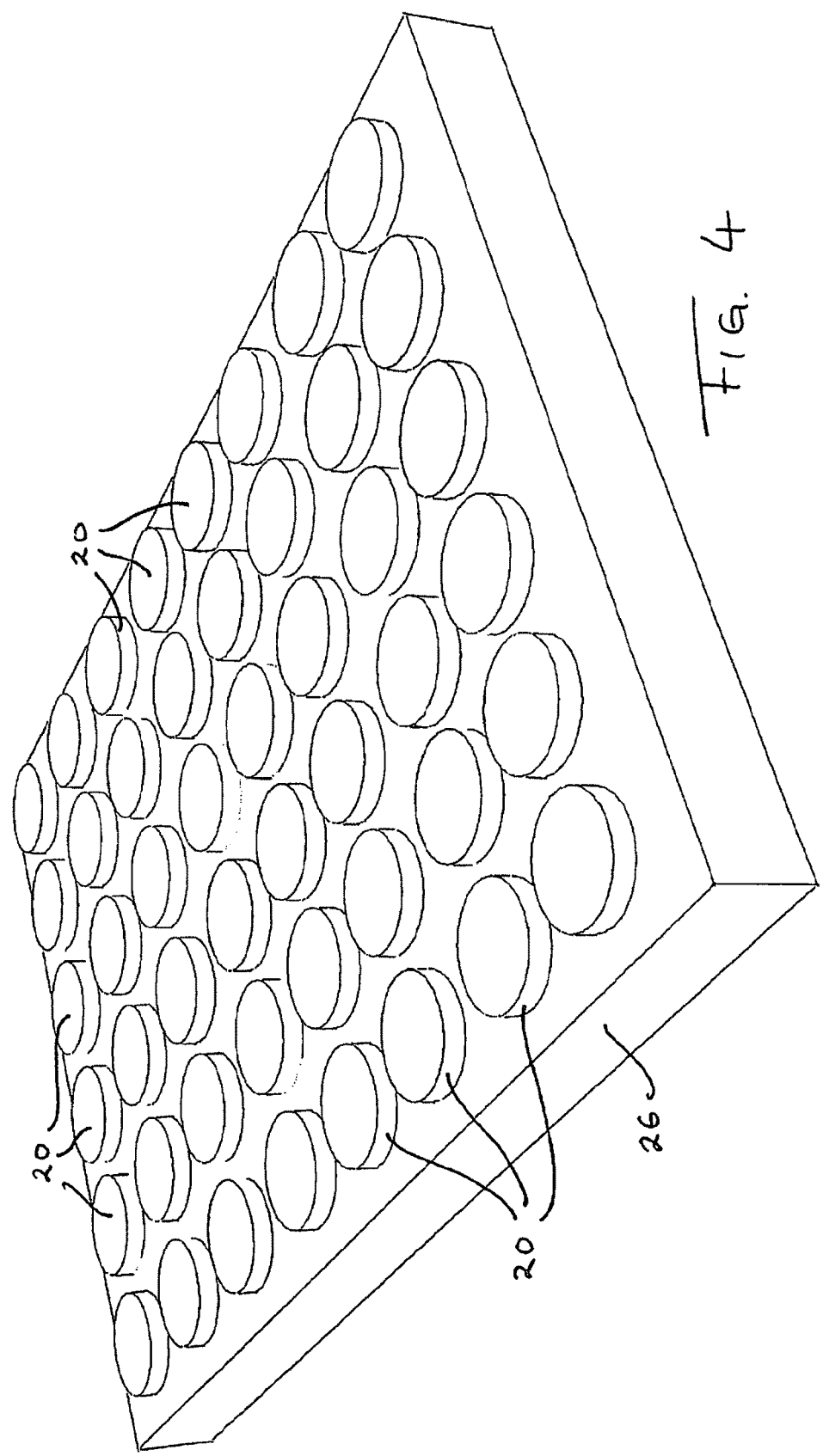

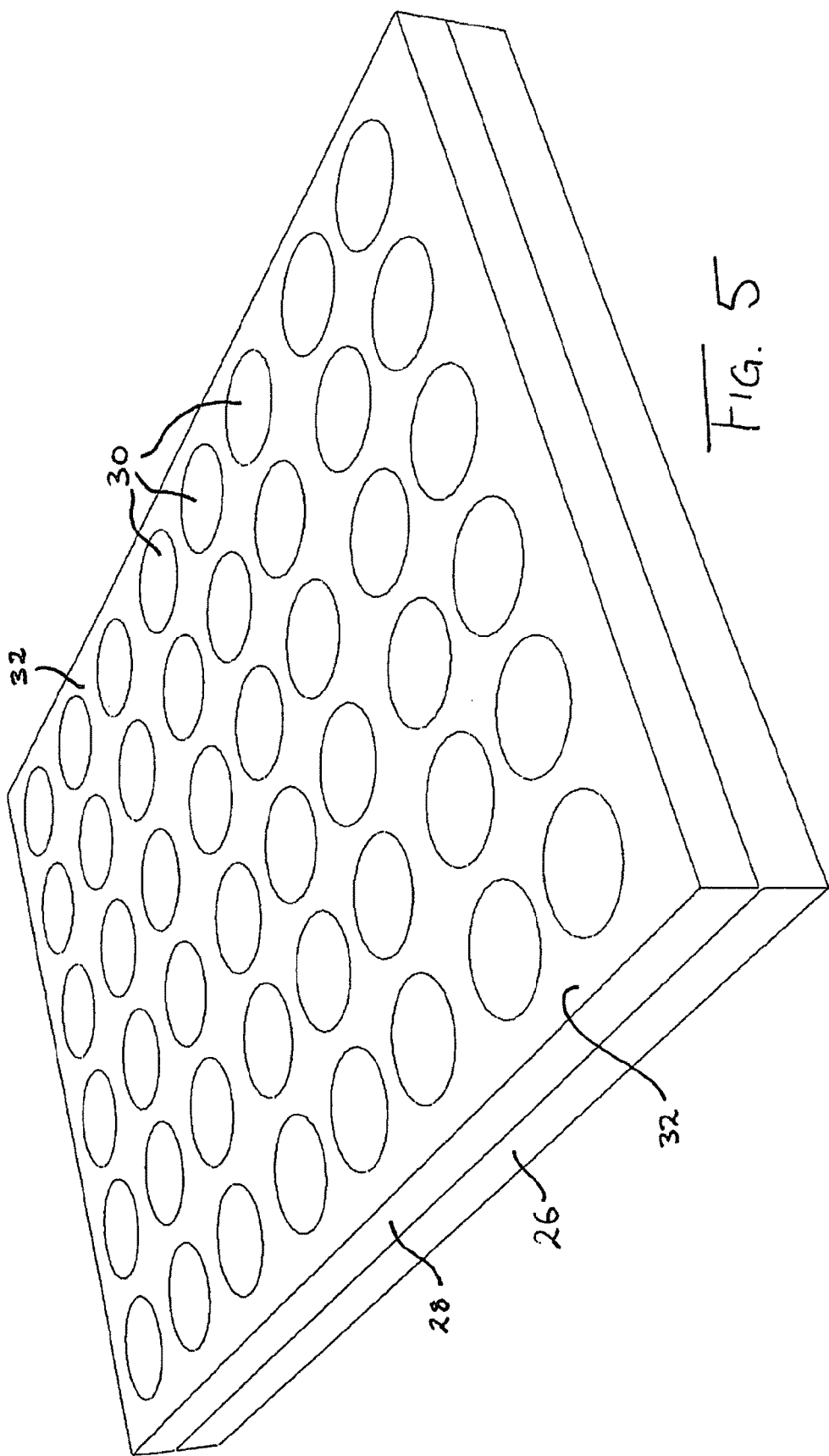

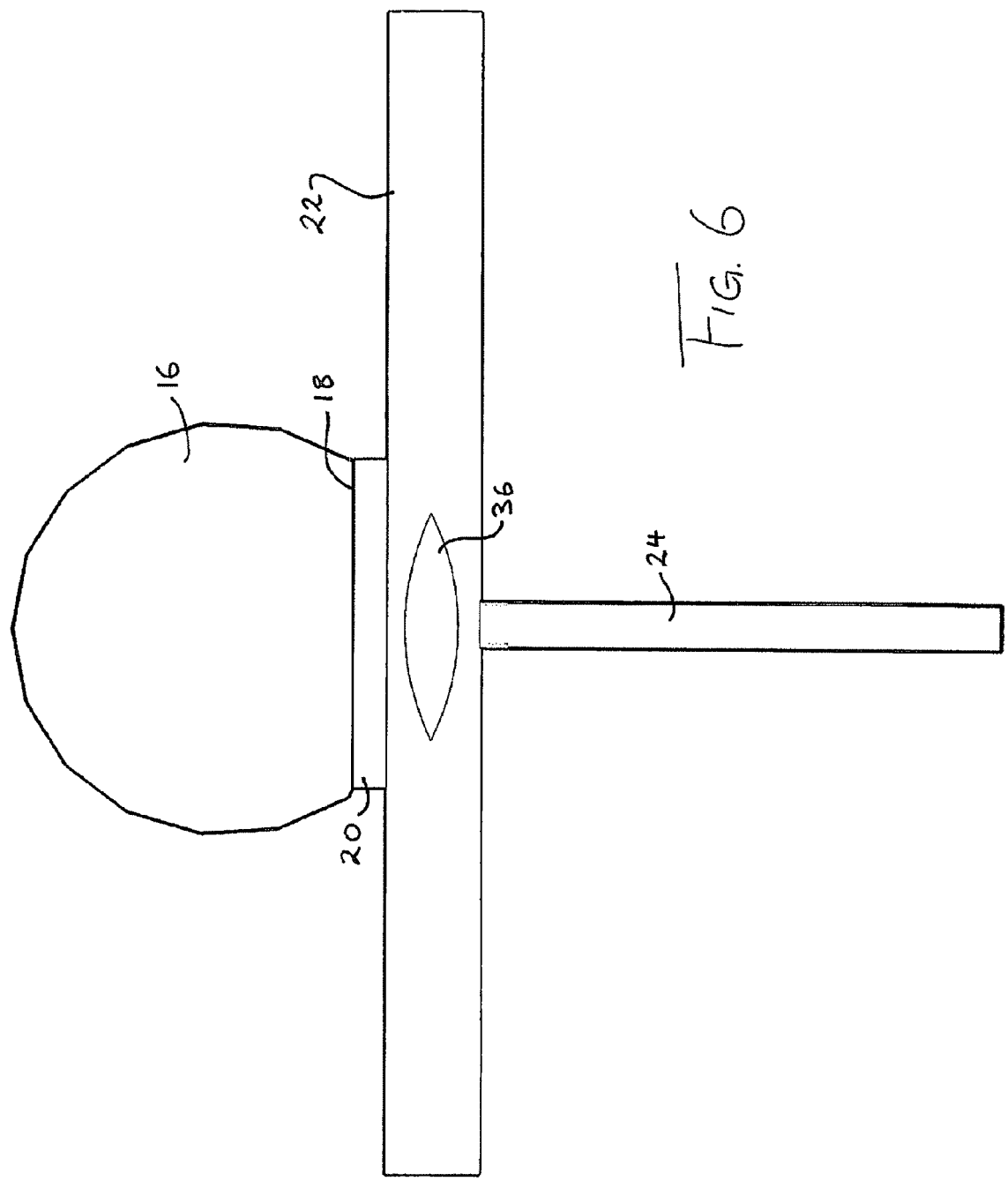

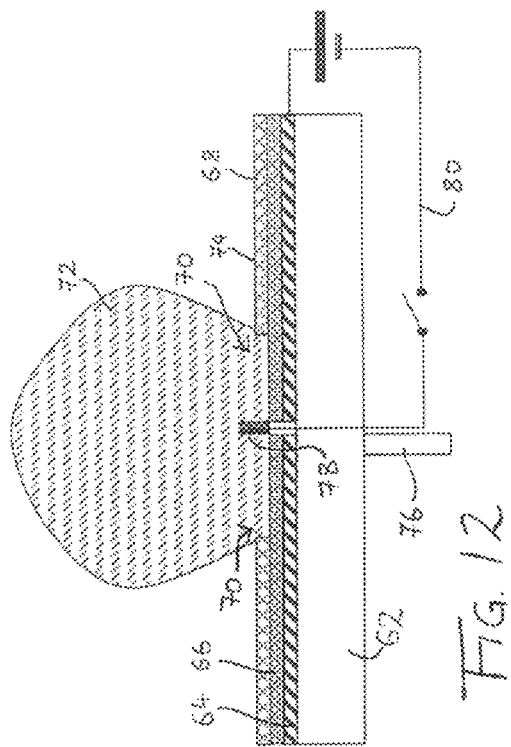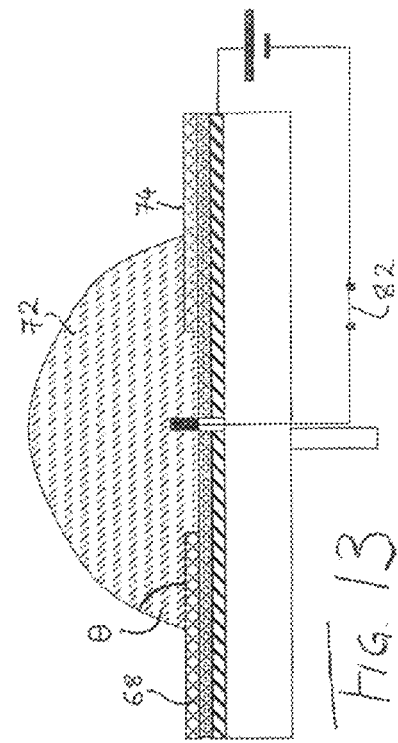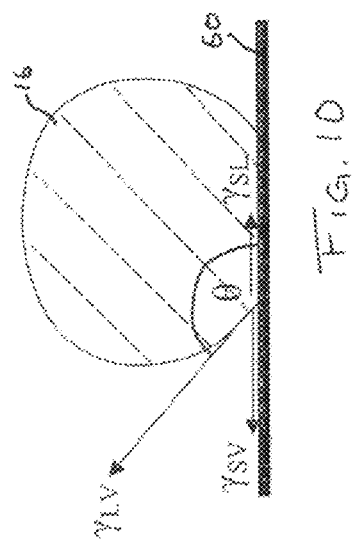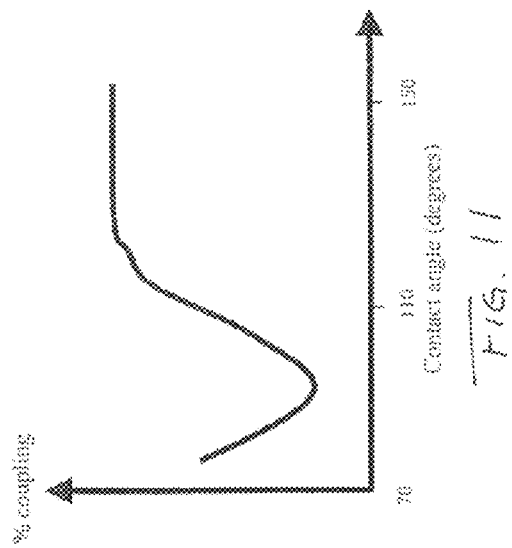

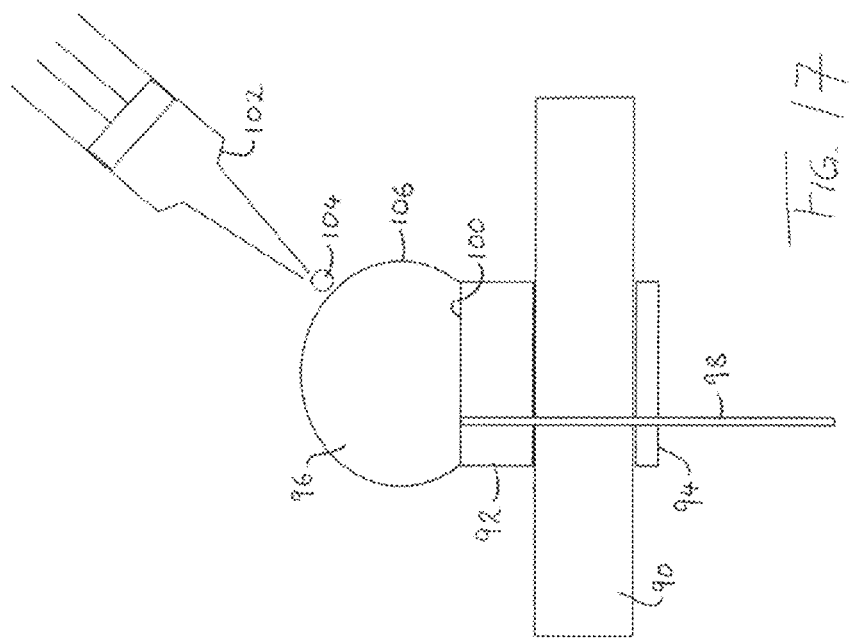
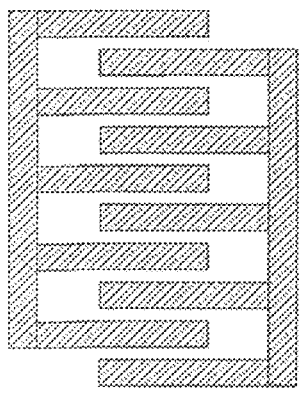
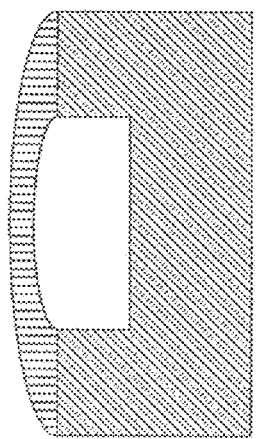
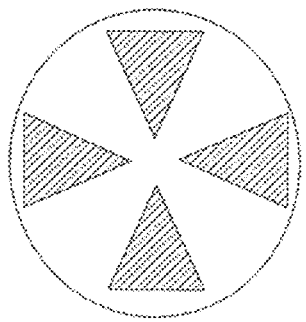

MICROVOLUME ANALYSIS SYSTEM

TECHNICAL FIELD

This invention relates to analysers for liquids, and in particular to spectrophotometers adapted for use with small volumes of liquids to be tested.

BACKGROUND ART

Various spectrophotometers are known in the prior art, which employ bulk liquid samples such as in vials or tubes. Such systems are unsuitable for many types of measurement in which small liquid volumes are to be analysed.

U.S. Pat. No. 6,628,382 and U.S. Pat. No. 6,809,826 disclose systems for handling small drop volumes. These systems have several drawbacks because they involve many automated moving parts such as swing arms, are difficult to effectively clean between samples because the samples are supported in the middle of complex machinery, and appear to be expensive to build and sell.

The present invention aims to overcome these difficulties and to provide greater measurement capabilities than these less versatile instruments.

DISCLOSURE OF THE INVENTION

The invention provides an analyser comprising a source of electromagnetic radiation, a detector for said radiation and a drophead comprising a surface which is adapted to receive a drop of liquid to be tested, the drophead being positioned in use relative to the source and detector to illuminate a drop received thereon and to cause an interaction in the path of the electromagnetic radiation between the source and detector, characterised in that said surface of said drophead is dimensioned to constrain the drop to adopt a shape which is dominated more by surface tension forces than by gravitational forces.

The analyser of the present invention relies on the phenomenon of surface tension to ensure a reproducible drop shape for a given volume. By dimensioning the drop-supporting surface to ensure that surface tension dominates over gravitational forces, the shape of the drop—and hence its interaction with radiation—is reproducible for a constant composition. In this way, differences in composition giving rise to different optical properties can be more accurately measured.

In one embodiment, said surface of said drophead is dimensioned to receive a maximum drop size of less than 10 microliters.

Preferably, the surface of said drophead is dimensioned to receive a maximum drop size of 0.5 to 5 microliters, more preferably in the range of 1 to 4 microliters. A currently preferred drophead supports a maximum drop volume of about 3 microliters.

Preferably the analyser further comprises a mounting body on which said drophead is mounted.

In this way, the mounting body can be used to support a very accurately machined drophead, and the mounting body can also be used to accommodate the optical and peripheral components of the system. In some instances, the mounting body can itself form part of the optical system, such as when the drophead is mounted on a semiconductor substrate having integrated optical elements.

Preferably, said drophead is transparent to said electromagnetic radiation and said source and/or said detector comprises an optical fiber terminating below said surface of said drophead for transmitting and/or receiving said electromagnetic radiation to and/or from said received drop of liquid through said transparent drophead.

When a mounting body is employed, the optical fiber can be mounted in said mounting body and terminate at an interface between the mounting body and the drophead.

There may be a plurality of said dropheads mounted on said mounting body. Such analysers are particularly useful in automated "array" systems for measuring multiple samples.

Preferably in such cases the analyser includes a plurality of said detectors, wherein each of said dropheads has one or more of said plurality of detectors associated therewith.

More preferably, each of said dropheads has one or more of said plurality of detectors associated exclusively therewith.

In particularly preferred embodiments, said mounting body comprises a solid state detector array and said detectors are individual detection elements of said array positioned to receive electromagnetic radiation from said dropheads.

Preferably, said solid state detector array is selected from a charge coupled detector array, and an array of diodes.

Alternatively, said mounting body can comprise a plurality of optical fibers each mounted within said mounting body to receive electromagnetic radiation from a respective drophead.

In some embodiment, said drophead comprises a plurality of drop-supporting surfaces isolated from one another by one or more structural features adapted to confine a drop to a single drop-supporting surface.

The structural features can comprise a surface region of different hydrophilicity than the plurality of drop-supporting surfaces, whereby said liquid drops are confined to the drop-supporting surface with which they have an affinity and are repelled from said surface region of different hydrophilicity.

The structural features can comprise surface discontinuities defining the plurality of drop-supporting surfaces, such that surface tension forces confine the drops to said drop-supporting regions bounded by said surface discontinuities.

Optionally, the analyser can include a microlens positioned below said drop-supporting surface for focussing radiation to or from said source and/or detector, respectively.

In certain embodiments, the analyser includes one or more electrodes adjacent the drop-supporting surface which when suitably energised cause the physical shape or position of said received drop to alter, thereby enabling the characteristics of the drop to be measured in different shapes or positions.

The analyser can include means for vibrating the drop, which may be for example an oscillator coupled to a piezoelectric structure associated with the drop-supporting surface, whereby suitable energisation of the oscillator causes the piezoelectric structure to vibrate a drop supported on said surface. It may also be an ultrasonic generator for coupling ultrasound energy into the drop.

Optionally, the analyser has a conduit for feeding a liquid to or from said drop-supporting surface to thereby allow the volume of a drop on said surface to be varied.

Alternatively or additionally, deposition means are provided for depositing a further liquid on the surface of a drop supported on said drop-supporting surface.

Preferably, the deposition means is controllable to deposit an amount of further liquid calculated to produce a monolayer.

The source and detector are preferably positioned relative to the drop supporting surface to deliver said electromagnetic radiation to said drop along a path causing a portion of said radiation to travel as a surface guided wave along a part of its path between the source and the detector.

Preferably in such cases, said path between said source and said detector, including said surface guided wave path, form part of an interferometer arrangement allowing variations in the length of said path to be calculated to within an order of magnitude of the wavelength of said radiation.

The drophead can include a reflective portion adapted to reflect radiation passing through the drop between the source and the detector whereby said radiation traverses the drop twice, first from said source to said reflective portion via said drop and then from said reflective portion to said detector via said drop.

The drop-supporting surface can be formed in a well structure within a drophead.

Preferably, the drop-supporting surface is elongated along one axis and wherein said source and said detector are positioned to direct light through said drop generally along said axis.

The analyser preferably also includes a housing generally opaque to said electromagnetic radiation.

The housing can be adapted to open to allow access to said drop-supporting surface and to close to shield said drop from external radiation during measurements.

In some embodiments, said source is mounted above the drophead and is adapted to transmit said radiation as a wavefront approaching said drop-supporting surface at a non-zero angle.

The invention also provides a method of analysing a liquid comprising the steps of:
a. supporting a drop of said liquid on a drop-supporting surface which is dimensioned to constrain the drop to adopt a shape which is dominated more by surface tension forces than by gravitational forces;
b. illuminating said drop with electromagnetic radiation; and
c. detecting said radiation following an interaction with said liquid drop.

Preferably, the method further comprises the steps of:
a. varying said drop by:
  i) applying an electromagnetic field to said drop to vary its position or shape;
  ii) varying the volume of said drop;
  iii) adding an analyte to the volume of said drop to vary its volume composition;
  iv) adding an analyte to the surface of said drop to vary its surface composition; or
  v) vibrating said drop to vary its shape;
and
b. detecting the effect of such variation on the interaction with the electromagnetic radiation.

Preferably, the step of illuminating said drop comprises coupling said radiation into said drop to create a surface guided wave and detecting said radiation as it emerges from said surface guided wave mode.

The method may also include the step of interferometrically determining a change in the pathlength of the radiation travelling as a surface guided wave within said drop.

Preferably the method further comprises the step of reflecting radiation emerging from said drop into said drop supporting surface back into said drop between the illumination and detection of said radiation.

The invention also provides in a further and independent aspect, a drophead for use in a drop analyser, the drophead comprising a drop supporting surface and one or more electrodes adjacent the surface which when suitably energised cause the physical shape or position of the drop to alter, thereby enabling the characteristics of the drop to be measured in different shapes or positions.

BRIEF DESCRIPTION OF THE DRAWINGS

The invention will now be further illustrated by the following descriptions of embodiments thereof, given by way of example only and with reference to the accompanying drawings, in which:

FIG. 3 is a perspective view of a third analyser;
FIG. 4 is a perspective view of a fourth analyser;
FIG. 5 is a perspective view of a fifth analyser;
FIG. 6 is a perspective view of a sixth analyser;
FIG. 10 illustrates a contact angle of a drop on a surface;
FIG. 11 is a graph of light coupling as a function of contact angle;
FIGS. 12 and 13 are side views of a seventh analyser;
FIGS. 14-16 are schematic illustrations of arrangements for vibrating a drop;
FIG. 17 is a side view of an eighth analyser.

DETAILED DESCRIPTION OF PREFERRED EMBODIMENTS

Figure 1:
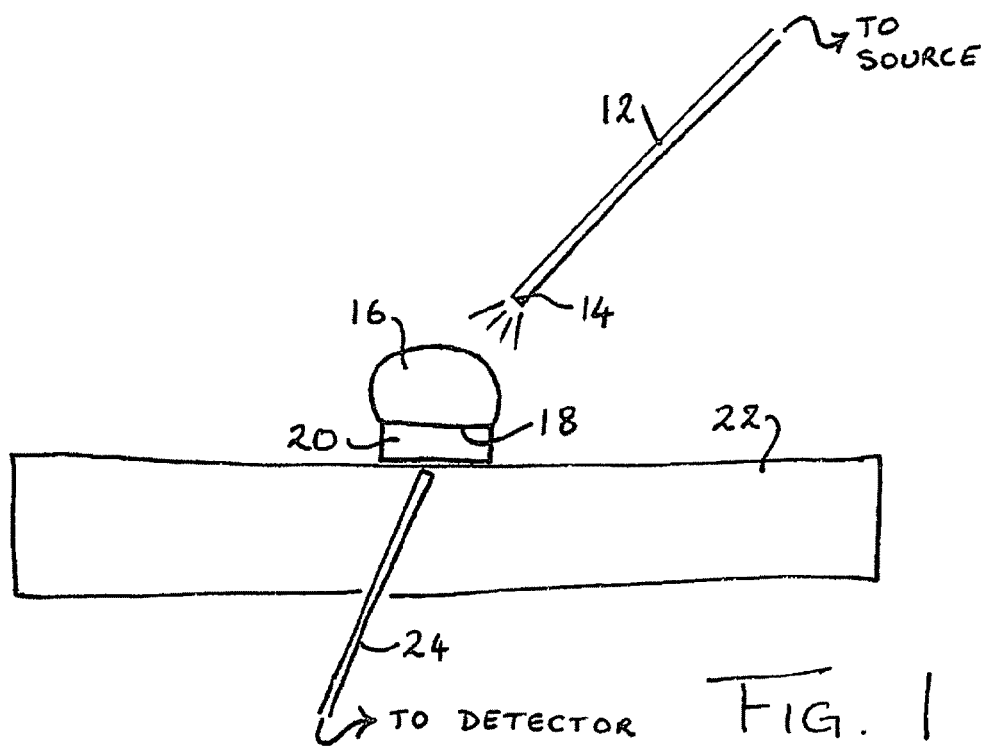
FIG. 1 is a side view of a first analyser.

In FIG. 1 there is shown an analyser having a source fiber 12 which is coupled to a source of electromagnetic radiation (not shown) and which emits such radiation at a free end 14 thereof. The source fiber is positioned to illuminate a drop of a liquid under test (LUT) 16 which is supported on a drop-supporting surface 18 of a plinth 20. The plinth 20 is formed of a material which is transparent to the frequency of electromagnetic radiation chosen to analyse the liquid under test 16. Examples include quartz, silicone oxide and glass.

The dimensions of the drop supporting surface 18 are chosen to ensure that the shape of the drop 16 is dictated by, i.e. dominated by, surface tension forces rather than by gravity. A typical plinth suitable for many liquids will have a cylindrical form, with radius 1 mm and height 1.5 mm, the upper circular face being used to support the drop. The plinth is bonded to a supporting platform 22 in which a detector fiber 24 is embedded or positioned. The detector fiber is positioned and angled relative to the plinth and the source fiber so as to optimise collection of photons from the source fiber through the LUT taking into account the geometry of the system.

While the simplest geometrical configuration has the source fiber vertically above the centre of the plinth and the collector fiber aligned with the source fiber beneath the plinth, such a configuration may require moving the source fiber in order to place a new drop of LUT on the plinth. It is for this reason that the embodiment shown in FIG. 1 has an angled source fiber and collector fiber, providing access to the plinth from above.

The fiber configuration may be reversed with the source fiber below the plinth and the collector fiber above the plinth.

Another option would include having the source fiber mounted in a lid of the apparatus which is opened to simultaneously move the source fiber out of the way and allow access to the plinth (e.g. to deposit a new drop), and which is closed to bring the source fiber back into position above that drop in a reproducible fashion, as well as to shield the drop from extraneous light sources (i.e. the instrument with its lid providing an enclosed dark space so that the only radiation being directed at the drop is that coming from the source fiber).

A further option would involve the plinth being slidably mounted so that it could be slid out of the region of the source and detector fibers and slid back in with a fresh drop in place.

Figure 2:
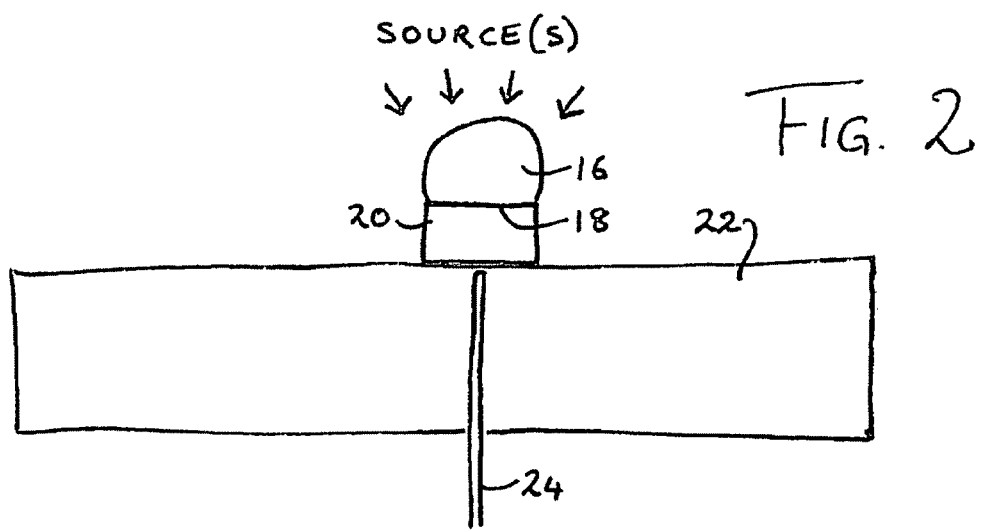
FIG. 2 is a side view of a second analyser.

FIG. 2 shows second embodiment in which a source fiber has been omitted. Instead a source of illumination (not shown) mounted generally above the liquid under test 16 couples electromagnetic radiation into the liquid under test, from where it passes through the plinth 20 and into the collector fiber 24.

A variation on the device of FIG. 2 is shown in FIG. 3, which is generally as described previously, but in which the plinth 20 is cuboid and the drop-supporting surface 18 (shaded for clarity) has dimensions of 3 mm×1 mm and a thickness of 1 mm. Such a plinth is suitable for supporting drop volumes of approximately 1-10 microliter. Other dimensions and shapes are possible provided that they also achieve the goal of ensuring a drop size in which surface tension forces dominate over gravitational ones.

FIG. 4 shows an embodiment of the invention in which an array of mass-produced plinths 20 are mounted on a charge coupled device (CCD) 26 or an active pixel sensor (APS), also known as a CMOS sensor.

These types of sensor are well known and enable more sophisticated image processing and intensification software and other technology to be used to enhance the amount of information available to the system.

Further embodiments of this concept could be to fabricate plinth structures over the individual detection elements of integrated structures such as CCDs, PIN Diodes or Avalanche Photodiodes (APDs). This could be carried out in a number of ways such as with a full custom design, the plinth for the drophead could be fabricated from typical IC fabrication films such silicon dioxide, silicon nitride, oxynitride or some of the commonly used polymers such as Polyimide, BCB or PMMA. There would also be the option of taking commercially available dies or wafers containing the CMOS devices and then carrying out post-processing at the die level.

The array could alternatively be manufactured using fiber detectors under each plinth. Arrays of plinths could be fabricated using MEMS fabrication techniques where numerous plinths could be fabricated on the top surface of a silicon wafer and "through holes" etched from the backside of the wafer, through which fibers could be placed in close proximity to the frontside plinths.

The system can be used with either a spectral-broad band source or narrow band source such as a LED/laser.

FIG. 5 shows an embodiment similar to FIG. 4 in that it employs a CCD sensor 26 to collect photons from droplets deposited on drop-supporting surfaces 30. However, rather than having the drop-supporting surfaces defined by an upper edge of a plinth mounted on the CCD 26 (as in FIG. 4), the CCD is overlain by a quartz sheet 28 on which the drop-supporting surfaces 30 are revealed as uncoated (and hence hydrophilic) regions surrounded by a coating 32 of a hydrophobic material. The change of the surface from a hydrophobic to a hydrophilic can be achieved with silanization chemicals. Quartz will not sustain a drop of low surface tension liquid such as methanol. However, with silanization such surfaces can then support the drop. The same technique, however, can be used to create drop-supporting surfaces for other liquids to confine the drop so that it is dominated by surface tension forces. This arrangement would be for aqueous drops and the reverse situation might be used for other liquid types.

Vapour deposition of chlorosilanes in selective areas on the quartz plinth sheet could result in hydrophobic areas covered by these monolayers and hydrophilic areas consisting of quartz or silicon dioxide. This could be achieved using a mask to form the areas that require functionalization. Asahi Glass Company of Tokyo, Japan, sell a suitable hydrophobic fluorocarbon polymer under the trademark Cytop, which may be more durable than the silanes mentioned above.

Alternatively, one might consider using for the plinths some low friction plastics such as Teflon (Teflon is a trade mark of E.I. du Pont de Nemours and Company of Wilmington, Del., USA) or COC (cyclic olefin copolymer), a highly UV-transparent plastic available from, for example, Topas Advanced Polymers of Frankfurt-Höchst, Germany.

In considering the suitability of various materials for the drop supporting surface or underlying structure, one must consider various issues as to the UV transmission vis-à-vis the drop forming properties and compromise on these matters in a suitable trade off. Quartz is an ideal material as regards UV transparency, and is preferable over many plastics whose durability is problematic for some liquids, i.e. they can be badly eroded both by aggressive chemicals and indeed proteins.

Plastics however can be more easily moulded and disposable platforms with raised plinths, having an appearance similar to the array version of this embodiment shown in FIG. 3, could be manufactured at low cost. The accuracy of manufacturing plinths with known diameters in such mouldings could be a real problem for some applications, but for relative measurements such as discussed below this should not be a problem.

As already mentioned, the detector pixels for the devices of FIGS. 4 and 5 can provide important intensity information about the focusing properties of the LUT. Such intensity distributions will be useful in studying the LUT in many situations. For sessile drops of known volume and shape, the physical properties of the liquid such as refractive index could be obtained from such information.

The scale of the device is crucial in this respect. By providing a drop-supporting surface of a size which constrains the drop to be dominated by surface tension forces rather than by gravity, the shape of a drop of known volume will be highly reproducible. Delivery of microliter-scale droplets is well established technology and thus the use of such small plinths ensures that both the size and the shape of the drop is highly reproducible allowing the refractive index and other optical properties of the LUT to be accurately and reproducibly determined.

Because light is reversible, the geometry of any of the said embodiments can of course be reversed in many situations.

FIG. 6 shows a schematic arrangement of a further embodiment in which light from a source (not shown) is coupled through a droplet of liquid under test 16 whose shape is principally determined by its volume, its surface tension and the geometry of a drop-supporting surface 18 on which it rests. The drop-supporting surface 18 is the upper surface of a quartz plinth 20 which is mounted on a platform 22 as previously described. As previously described also, a collector fiber 24 receives light coupled through the droplet 16 and plinth 20. A microlens, shown schematically at 36 is positioned below the plinth to collect the light and couple it to the collector fiber 24. Microlenses can be fabricated through a number of IC/MEMS related techniques such as the use of a LIGA process (German acronym for the use of X-Ray Lithography, Electroplating and Moulding) or the use of greyscale masks and an etch process or the use of a varying intensity E-beam lithography and etch process.

These lenses could be placed under a plinth and in the light path to a collecting optical fiber through a number of MEMS processing methods. One possible but not exclusive process route is to fabricate an array of microlenses on one wafer and a corresponding array of plinths on another wafer. A cavity is created behind each plinth on the plinth wafer using deep reactive-ion etching (RIE) techniques, and then the micro lens wafer is bonded to the plinth wafer so that the lens is inserted behind each plinth. Finally, a further etched channel can be etched into the backside of the microlens wafer to create an insertion guide for a collecting optical fiber.

Light can be supplied by any source: pulsed or continuous; UV, IR or visible; laser, LED, spectral, deuterium, xenon, tungsten sources, etc. It can be seen that the light is coupled by the droplet into the collection system. Again, because the drop is so small, any repeatable volume deposited on the drophead will be constrained by this dominant surface tension forces to the same repeatable shape given this is much greater than the distorting gravitational force, and thus the coupling of light, or reflection inside of the drop, will be reproducible due to the reproducible shape of the drop. This means that any differences in observed spectrum are due necessarily to the inherent liquid characteristics, not to any changes in dimensions or drop shapes. Reproducibility of drop shape means that the integral pathlength (a factor in Beer's Law calculations) is potentially more accurate than in other systems. The situation is such that employing a pulsed UV source, bulk fluorescence can be excited and the fiber used then to collect visible photons from the fluorescence decay.

Figure 7:
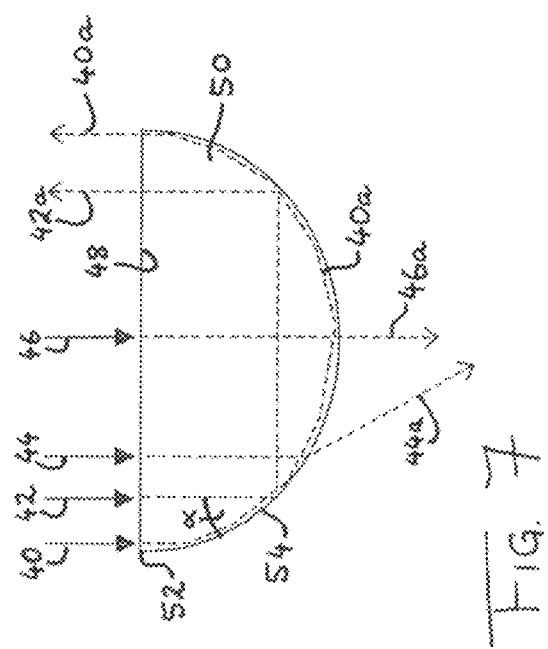
FIG. 7 is a ray tracing side-view diagram of a plane wave illuminated drop.

FIG. 7 is a ray tracing diagram showing the paths taken be four incident rays 40, 42, 44, 46 impinging on the planar surface 48 of a hemispherical drop 50.

Ray 40, which enters the drop almost at the circumferential edge 52 follows a path 40*a* which grazes the hemispherical curved surface 54 of the drop 50. It thus emerges at a diametrically opposite point in the opposite direction to that which it entered.

Ray 42 impinges on the hemispherical surface 54 at a much greater angle of incidence alpha. While constrained by total internal reflection (as for ray 40) it makes only a couple of reflections before emerging at a diametrically opposite point as ray 42*a*.

Ray 44 enters the drop even closer to the centre than ray 42, and at a point where the angle of incidence on hemispherical surface 54 is greater that the critical angle required for total internal reflection. Accordingly, ray 44*a* emerges through the hemispherical surface 54 at an angle determined by the respective refractive indices of the LUT and the surrounding medium.

Ray 46, which impinges on the planar surface 48 at its centre point meets the hemispherical surface 54 at the normal angle and emerges undiverted as ray 46*a*.

Figure 8:
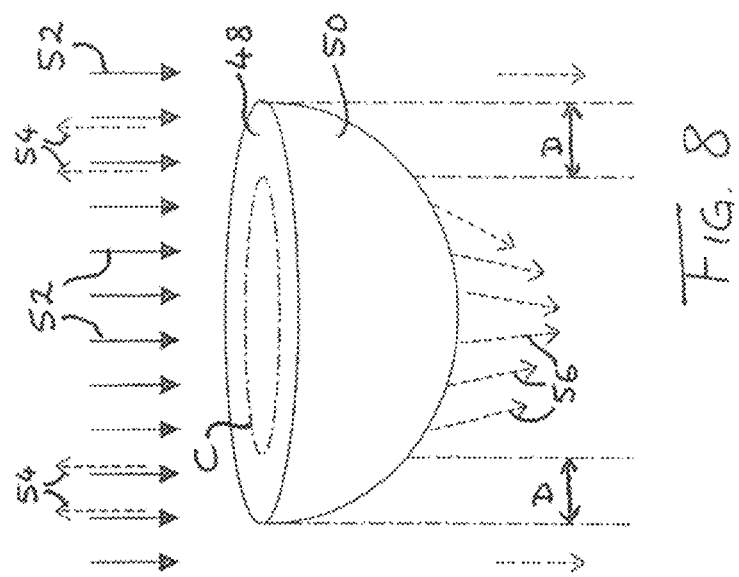
FIG. 8 is a ray tracing perspective-view diagram of a plane wave illuminated drop.

The three-dimensional picture is illustrated in FIG. 8. When a set of parallel rays 52 impinge on surface 48 of drop 50, there will be a critical distance D between the circumference of the drop and an imaginary internal circumference C. Impinging incident rays 52 which meet the surface in this annular region will be reflected back towards the source (not shown) as reflected rays 54 (as was the case in FIG. 7 for rays 40 and 42 which emerged reflected back as rays 40*a* and 42*a*, respectively). However, rays which meet the planar surface 48 within the circumference C of the imaginary circle, will meet the hemispherical surface at greater than the critical angle and will thus emerge through the droplet surface as refracted rays 56 (as was the case for incident rays 44 and 46 in FIG. 7 which emerged as refracted rays 44*a* and 46*a*, respectively).

When viewed from the direction of the source, therefore, the planar surface 48 of the droplet will be divided into two distinct regions, namely a bright annular band due to the reflected rays 54 (FIG. 8) emerging from the annular area between the circumferential rim 52 and the circumference of the inner imaginary circle C; and a dark area within that circumference C.

In mathematical terms, if the drop is hemispherical (a good approximation in many situations) and the refractive index of the LUT is $\eta_1$ and that of the second medium is $\eta_2$, then the inner radius of the circle defined by the circumference C (i.e. of the dark region) is $\rho = r_{hemisphere}(\eta_1/\eta_2)$ and the average reflectance of the circular region is $R = 1-(\eta_1/\eta_2)^2$. Clearly R increases with the ratio of the refractive index. Many simple geometric-ray and electromagnetic wave calculations can be used to derive refractive index of the LUT. Illumination can be from underneath the plinth or from above and fibers and many other optical arrangements can be arrived at in which to direct the light into or from the drop based on the various embodiments here and other optical configurations of source, detectors, cameras, etc.

The importance of measuring contact angle in surface science cannot be overstated. The problem with microdrops and surfaces such as those produced in IC fabrication are somewhat complicated but the Young-Dupré equation does not take into account the roughness of the surface.

The geometry shown in FIG. 10 illustrates the factors determining a contact angle between a drop 16 and a surface 60, resulting from a quasi-equilibrium balance between various surface forces, namely $\gamma_{SV}$ for the interface energy between the solid and vapour phases, $\gamma_{SL}$ for the interface energy between the solid and liquid phases, and $\gamma_{LV}$ for the interface energy between the liquid and vapour phases, (i.e. the surface tension).

The Young-Dupré equation gives the contact angle θ (the internal angle within the liquid body between the droplet surface and the supporting surface) as:

$$\cos \theta = (\gamma_{SV} - \gamma_{SL})/\gamma_{LV}.$$

This formula is modified for complex rough surfaces to include a roughness factor such that $\cos \theta_{rough} = r \cos \theta_{smooth}$ where the roughness factor r is always found to be greater than unity.

FIG. 11 shows that the light coupled into the drop and collected by the collector fiber here is a function of the contact angle for embodiments such as those of FIGS. 1 and 2.

FIG. 12 shows an arrangement in which a quartz platform 62 is coated first with a conductive coating 64 of highly conductive indium tin oxide (ITO) and then by an insulative coating 66 of parylene-C. A hydrophobic coating 68 covers the insulative coating 66 but leaves a window 70 exposed such that a droplet 72 placed onto the upper surface 74 will be confined to sit on the window by the hydrophobic coating 68. A collector fiber 76 underneath the quartz platform collects light coupled into the droplet from a source (not shown).

The droplet assumes the form of a truncated sphere by virtue of its volume, the surface tension and the hydrophobicity of the coating 68. An electric circuit 80 is provided between the conductive coating 64 and an electrode 78 which contacts the droplet volume within the window 70.

As shown in FIG. 13, when a switch 82 is closed to complete that circuit, electrostatic attraction draws the droplet 72 down onto the surface 74 of hydrophobic coating 68, changing the contact angle θ and hence the optical properties of the droplet.

Varying the voltage applied to the electrode in the drop makes it possible to produce a variation in drop profile. The problems associated with cleaning such an arrangement can be improved using IC fabrication techniques to produce a conducting path to a central metallised region at the centre of this drop rather than the electrode as shown in FIGS. 12 and 13. It is important that appropriate choices are made to enable cleaning of the surfaces that may be contaminated by enzymes or proteins for example. Aluminium and gold are widely used but may not provide longevity in fabricated structures that may be attacked by chemicals. An alternative conductor such as polysilicon is an option.

The arrangement shown in FIGS. 12 and 13 can be varied for improved injection and collection of light to and from the drop via fibers. These fibers can be placed symmetrically in this drop head, e.g. close to the two arrows 70 in FIG. 12 just inside the drop of the minimum base diameter. As in the case of all the embodiments described in this patent, it would be best if the fiber ends did not protrude through and touch the liquid of the drop, but were rather placed in blind holes that are close to the surface and insulative coating 66. The use of quartz for the platform would be the best material of choice for the platform 62 if UV operation is required for the analysis.

An electrostatic-tensiotrace would arise if the voltage on 78 was ramped up in a uniform way to cause the drop to spread from the shape shown in FIG. 12 to that shown in FIG. 13. If the drop was then pulled back from its position shown in FIG. 13 to that in FIG. 12 by reversing the voltage ramp then a tensiotrace having a slightly different form than a conventional tensiotrace would be obtained. The ramp would give a reverse tensiotrace with a rainbow type peak occurring in the FIG. 13 drop shape and the highest order peak in the tensiotrace appearing with the drop shape shown in FIG. 12. All the normal measurements associated with tensiography would now be possible with such an arrangement, but would be achieved with a fixed volume of liquid and could properly be termed isochoric tensiography to differentiate this approach fundamentally from the traditional form of tensiography with changing (generally increasing) volumes being the driving process to change the tensiotrace.

Figure 30:
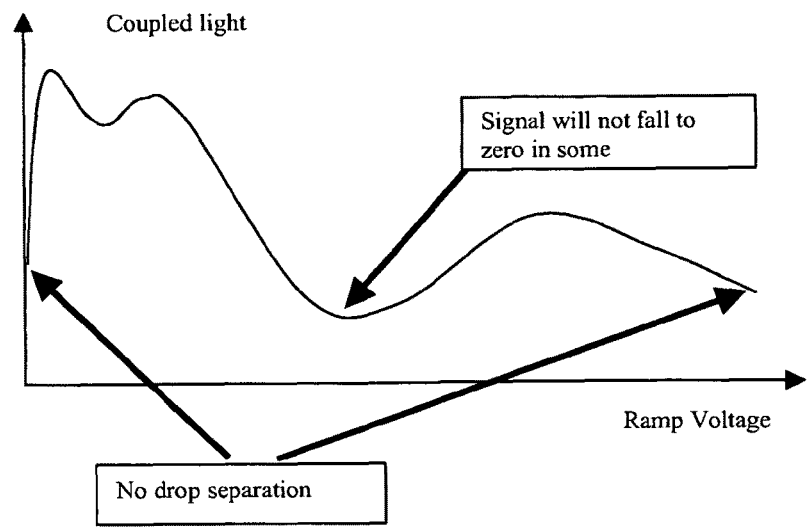
FIG. 30 is a graph of coupled light as a function of applied voltage in the embodiment of FIGS. 12 and 13.

FIG. 30 shows a tensiotrace achieved with this arrangement, in which the first peak is a fourth-order reflection, the second a third-order, and the third a second-order reflection. The latter in classic tensiography is known as the rainbow peak.

It is of course possible to use vertical illumination outside the drop and just use a single collector fiber at say the centre of the drop. FIG. 11 shows that the light coupling measurement with such a collector fiber and vertical illumination could be used to determine contact angles over a considerable range of contact angles (here say 70° to)115° for our simple dropheads to provide an optical calibration signal for the electrowetting control. Thus, if a plate with a fiber positioned at a centre was used and drops placed at this position, a dynamic light coupling measurement should be calibratable to enable contact angle to be determined. In a static measurement there will normally be two contact angles for a given photometric signal value (i.e. 80 and 110 degree contact angles might each give the same photometric signal, but by noting whether the signal is increasing or decreasing, these can be distinguished).

It should be noted that also from such a measurement it should be possible to determine the refractive index of the LUT. Such a simple embodiment of a simple plate, central fiber and drop-centering arrangement with vertical illumination and a collector fiber beneath such as shown in FIG. 2 but without a plinth should enable UV-visible spectra, fluorescence spectra, contact angle and refractive index to be determined from a single drop.

Contact angle changes are made by varying the voltage of an electrode al la V. H. Kwong, M. A. Mossman and L. A. Whitehead in their paper entitled "Control of reflectance of liquid droplet by means of electrowetting", Applied Optics, Vol. 43, No. 4, 1 Feb. 2004. The study of contact angle is one thing that can be controlled in such an embodiment. The work of Varioptic in this area has provided technology developed by Bruno Berge for centering microvolume drops with patents, as detailed in http://www.varioptic.com/en/technology.php?cat=technotes.

In this embodiment, the changing of the shape of the drop under electrostatic voltage control, would greatly enhance the measurement capabilities of the microdrop analysis technique. The simplest explanation is perhaps given in "Microfluidics systems", (see http://www.physics.ubc.ca/ssp/research/microfluidic.htm). This reprise of the technology shows clearly that optical analysis of drops from measuring their reflectivity is useful and that this reflectivity varies with the electrical conditioning of the drop placed on a PCB with patterned electrodes, working with hydrophobic and hydrophilic surfaces. In principle, using such a system in conjunction with a fiber or fibers would enable all the usual tensiograph measurands of surface tension, refractive index, absorbance, and turbidity to be determined.

Surfactants, enzymes and proteins, and other surface (or partially surface-active) molecules move to the surface of drops. It is very important to have these molecules spectroscopically monitored and analysed. The illumination from above will be refracted into the drop. Various ray paths will couple light into the detectors placed in the plinth of this sessile drop. The fibers at the centre will receive light that passes through the bulk of the drop and will pass through a microscopically thin layer of the surface-active molecules of interest for this analysis. There will be some of the rays incident on the drop that will be refracted into this surface layer. These will be surface guided around the drop and will be collected by the fiber situated just inside the edge of the drop. This signal will contain spectral information on the surface-active molecule. The difference between the two signals could be considered separately, or it may be advantage to look at the difference signal between absorptions in the bulk and surface spectra.

Figure 31:
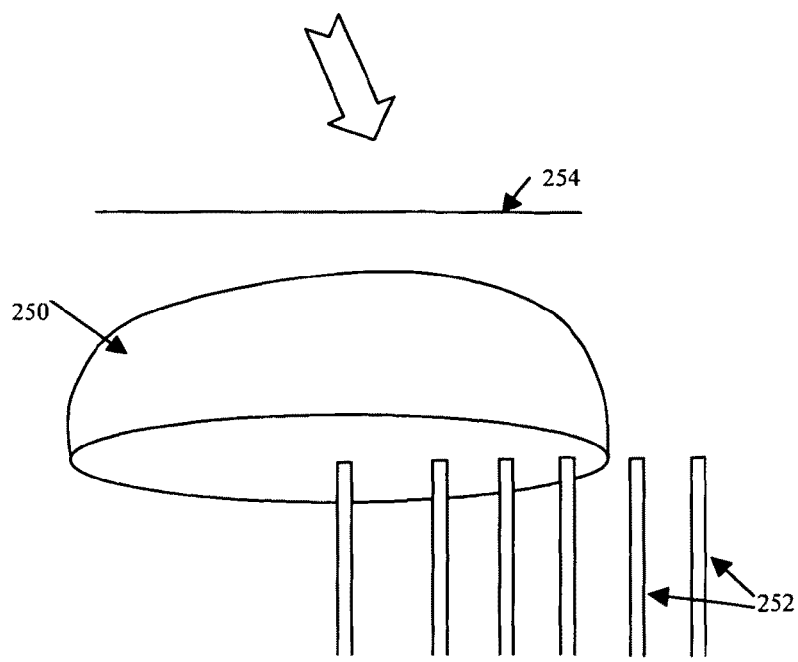
FIG. 31 is a schematic view of a further analyser.

Such an arrangement, see FIG. 31, of an illumination system above the drop of the LUT and a series of fibers 254 connected to CCD or CMOS spectrophotometers would be a suitable arrangement for differentially measuring the light that was passing close to edge of the drop 250, and the light that was near the centre. The illumination situation would need to be experimentally adjustable with some means of tilting the angle of illumination to maximize the coupling into the surface. The illumination system can be considered as a wave front 252 that is parallel to the drop base, as shown in FIG. 31. The surface wave would almost certainly be optimised by tilting this wavefront such that the left hand side is lowered with respect to the leading right hand edge. The array of fibers could all be perhaps taken to a CCD or CMOS detector capable of simultaneous multiple spectral recordings of the same chip. Such equipment is available from Spectral Signatures in University College Dublin (http://www.ucd.ie/spectral/).

The reversal of the situation could be simply devised with illumination from substage using fibers in the same positions. In this situation the rays are similar to those shown in FIGS. 7 and 8 but with internal reflections now coupling the light from the left hand side of the drop, to that on the right hand side where the collector fibers are situated. The collimation of light is useful, but not essential for such measurements, in most situations it is very simple to determine the angles of illumination and if this divergence of illumination ray angles is known, then such measurements as described here are easily interpreted and modeled.

Figure 9:
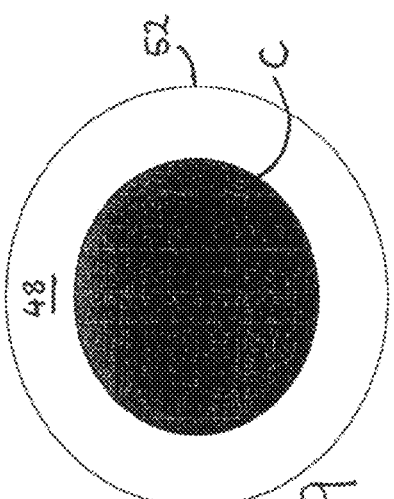
FIG. 9 shows the illumination pattern seen from the illumination side of said drop.

FIG. 9 shows a situation in which this has been explained in the Kwong, Mossman and Whitehead paper above. The very distinct bright and dark region in the drops in this electrowetted pixel array (FIG. 13 in their paper) mean that differential measurements can be done between the regions by simply viewing the image of these drop arrays with cameras. Such differential measurements could have great value in some analytical situations. The fact that an array of microstructures can be manufactured is also useful. If a device has enough such measurement plinths then it might make it possible to avoid any cleaning of the plinths and use this device as a disposable analysis element. Such situations might be important say in medical applications with infectious liquids.

Measurement could be made from measuring the geometry of (say) the dark region in these drop images, from measuring and quantifying reflectivities in the various differentiated regions of these images, or from conducting spectral analysis of light from a region of the microvolume droplet or other ways that come from simple optical measurement embodiments of this rather geometrically simple optical entity. The most important thing however is that with several fibers or other types of detectors above or below the drop of the LUT differential measurements can be made that will enable differential bulk-surface analysis to be undertaken.

The LUT can be caused to vibrate in order to affect mechanical disturbances of the sessile drop. Such vibrations could be studied from the pixel array beneath the drop, for example, and used to investigate the rheology of the LUT. The variation in optical signal with various excitation frequencies and amplitudes could profile these rheological properties of the LUT.

An alternative idea for optical monitoring of the drop would be to use an LED in the substage to produce light injection into the drop. This retro-illumination system might overcome fabrication problems with fibers.

If this does not work illumination from above would be a practical option. This would not give such beautifully simple geometric bright-dark differentiation of the regions, but would give a geometrical situation that could be understood geometrically. Camera images could be used then to view the forced oscillations of the drop and their affect on the differentiated regions in the drop. The dark region in this situation would be the reverse of that with retro illumination with light centre regions and dark edge to the drop.

It is possible to create a vibrating surface using a combination of IC fabricated dropheads integrated with a transducer. For example by fabricating a simple voltage controlled oscillator and integrating this with a transducer such as a vibrating cavity or capacitor or via an interdigitated metal comb structure to a piezoelectric material as in a surface acoustic wave (SAW) device, the electrical signal can be translated into a physical vibration.

The vibrations may be ultrasonic. The use of ultrasonic excitations might be helpful in certain bio-assays in which it was, for example, important to degas the sample and note the effect of the change of composition with respect to a dissolved gas on the mobility or activity of say a protein, enzyme or important bio-molecule, or to denature these biomolecules and thus change/control the conditions of the specific assay or process in a useful way.

FIG. 14 shows an interdigitated comb structure for use in a SAW-type device as described above. FIG. 15 shows a polysilicon cavity on oxide structure in cross-section, while FIG. 16 shows the same structure in plan view from above showing the electrodes on the top surface.

These devices work by piezo excitation. The comb structure of FIG. 14 made of the piezoelectric material pulls the wafer surface together and apart, hence inducing resonance. One example of an interdigitated comb structure is disclosed in U.S. Pat. No. 7,053,523. The polysilicon cavity on oxide of FIG. 15 has the four electrodes fabricated in a cavity. The differential pull from the wider region to those of the tip of these electrodes will induce a differential mechanical stress. The cavity itself of course has a resonance frequency and thus if the piezo excitation is at the right frequency the whole structure will resonate. Different sized cavities can be designed to produce different frequencies of operation.

FIG. 17 shows a further experimental arrangement of some current importance. There may be many such variations on this theme of course, but this example is one that will illustrate the general nature of such experimental set-ups. The analyser comprises a platform 90 bearing a plinth 92, and having a CCD detector 94 mounted below it to collect light coupled through a droplet 96 from a source (not shown). A capillary tube 98 extends to the drop supporting surface from below the device and is used to feed a volume of liquid to the drop supporting surface 100 to create the droplet 96 thereon.

A micro-syringe 102 adds a second liquid 104 onto the surface 106 of the droplet 96. The sample volume of the second liquid 104 is preferably calculated to say produce a monolayer or several such layers on the surface of the droplet 96. This experimental set-up can then be used to study the surface interaction of the second liquid 104 with the first liquid 96 or with further analytes introduced into the droplet volume via the capillary tube 98.

In one application the first liquid is water or an aqueous solution and the second liquid is a solution of cholesterol in methanol. By introducing various enzymes into the water droplet, their interaction with cholesterol can be studied. The spectroscopic analysis of the situation can be made with either UV-visible type transmission measurements or by exciting fluorescence from a UV source. It is to be understood that there may be in this and indeed any other embodiments discussed here any number of capillary feeds for adding drops to the head, cleaning the drophead, enabling special drop components to be added such as enzymes etc. The selection of microfluidic arrangements is independent of the optical criteria, though care must be taken to ensure that the optical arrangement is not adversely affected.

Figure 18:
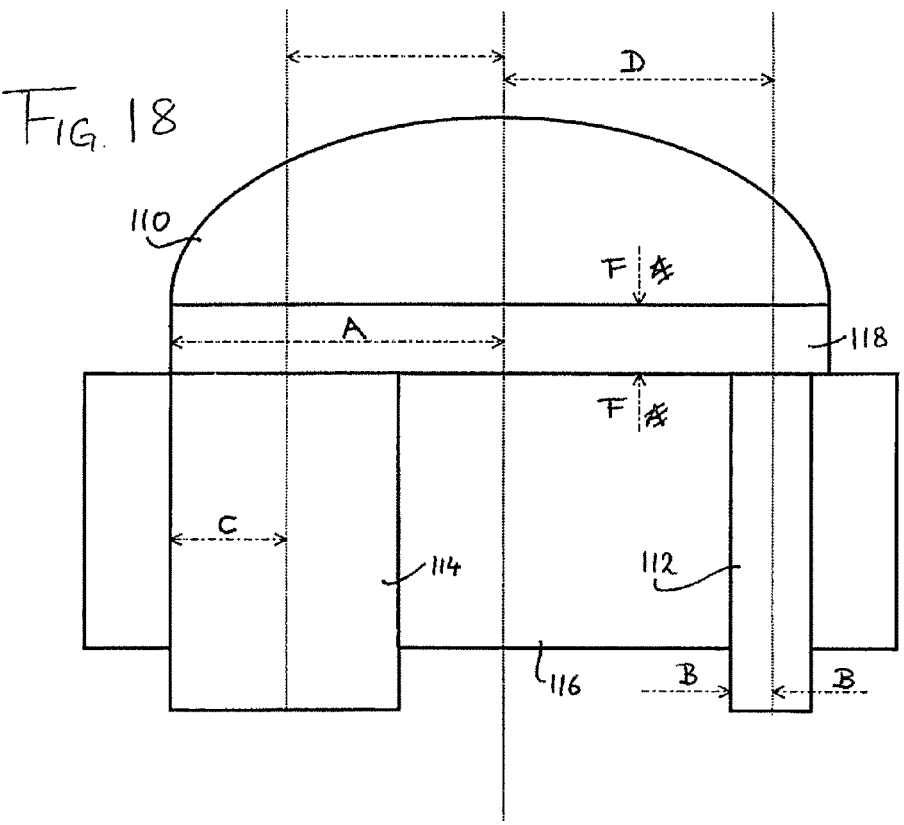
FIG. 18 is a schematic view of an analyser showing various labelled dimensions.

FIG. 18 shows a further arrangement for use in measuring surface characteristics of a droplet 110, with an input or source fiber 112 and an output or collector fiber 114 extending through a platform 116 and into a drophead or plinth 118 on which the droplet 110 rests. The syringe is not shown here but could be included.

Modelling work has shown that the optimum parameters for such a setup are as follows, with reference to the dimensions indicated in FIG. 18:

| Dimension | Description | Value |
|---|---|---|
| A | Radius of quartz disc | 0.75 mm |
| B | Radius of input (source) fiber | 0.05 mm |
| C | Radius of output (collector) fiber | 0.50 mm |
| D | Displacement of input fiber axis from the centre | 0.65 mm |
| E | Displacement of output fiber axis from the centre | −0.25 mm |
| F | Thickness of plinth | 0.50 mm |
|  | Maximum throughput | 2.8%-3% |
|  | Drop volume maximum | 0.7-1.0 μL |

Figure 19:
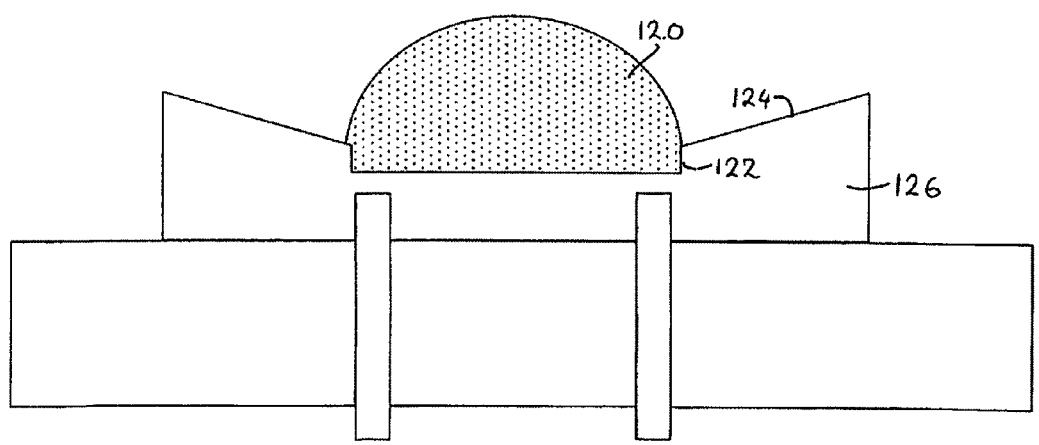
FIGS. 19 to 25 are side views of ninth to fifteenth analysers, respectively.

FIG. 19 shows a drophead wherein the drop 120 sits in a well 122 formed on the upper surface 124 of a fabricated silicon dioxide plinth 126 (which can optionally be capped with a quartz cap, not shown). Such a female geometry may provide practical benefits of analysis over a flat plinth. This arrangement might for instance offer advantages for surface guiding drop spectroscopy that has been mentioned above. Such arrangements could also be useful for a drop-on-drop arrangement designed to produce a liquid-liquid surface layer. The outer drop perhaps could be deposited on top of the initial drop and the two drops could be of immiscible liquid types. In the FIG. 19 arrangement, the surrounding unwetted area might be made hydrophobic in order to ensure measurement drops were constrained to the region of the recessed head.

In order to spectroscopically investigate the surface layer, source fiber 112 injects light into the droplet's surface layer. The collector fiber picks up the surface guided wave, which has been encoded with the UV absorption spectrum of the surface layer. In FIG. 17 the excitation could have been from pulsed UV above the LUT, but both arrangements are possible for studies of surface layer interactions.

Figure 20:
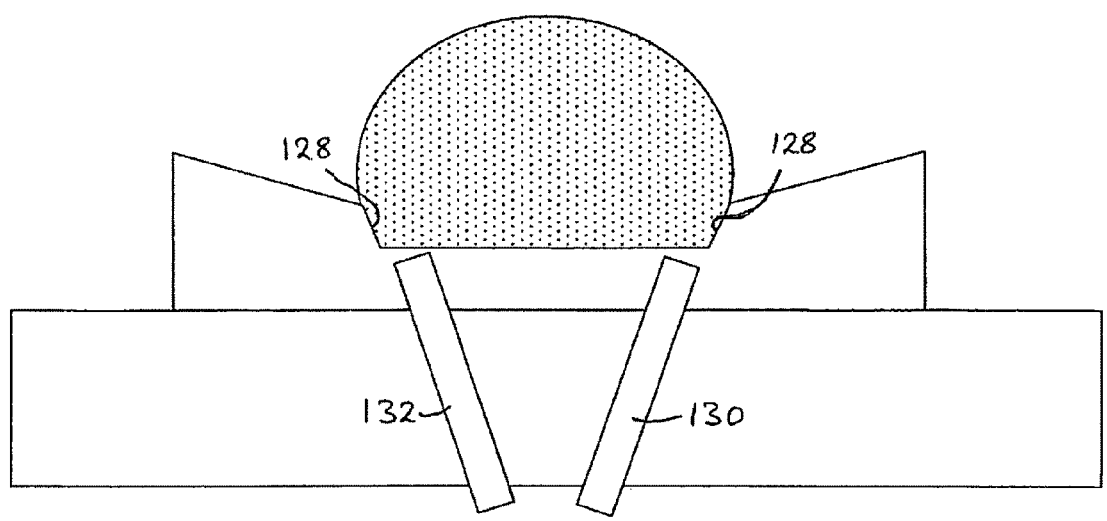

FIG. 20 shows a variation on the FIG. 19 drophead, with a sloping well edge 128 and in which the source fiber 130 and collector fiber 132 are angled to optimise the injection and collection of light into the drop surface layer along the angle defined by the sloping well edge 128. It is clear that the diameter of the collector fiber can be varied to improve collection efficiency as in case of FIG. 18.

FIGS. 21-24 show four further analyser configurations with different arrangements of source and detector. Each embodiment shares in common a plinth 132 from which a droplet 134 is suspended, and a capillary feed tube 138 for supplying the liquid for the droplet 134 to the drop supporting surface 136 of the plinth 132. It will be appreciated that the feed tube is optional and that the droplet may equally be placed on the surface using a syringe or other liquid deposition apparatus. Similarly, while the arrangements of FIGS. 21-24 are adapted for pendent drops, they can be inverted and used for sessile drops.

Figure 21:
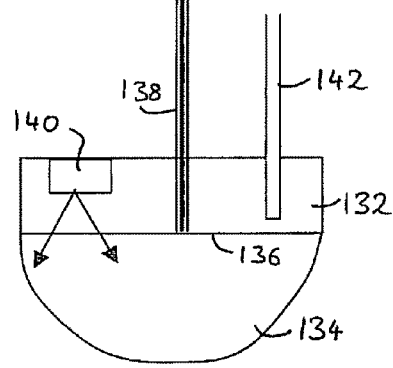
Figure 22:
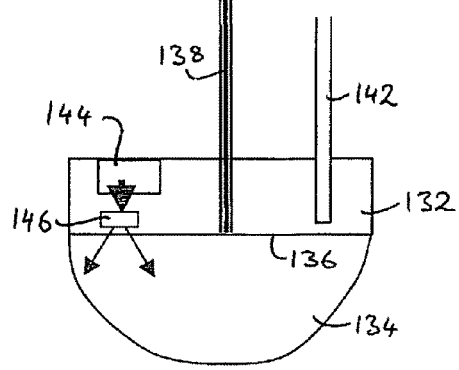

In FIG. 21, the source is a white LED 140 and the collector is a fiber 142. In FIG. 22, the LED is replaced by a laser 144 which illuminates a diffuser 146. Either of these two embodiments shows a single collector fiber but multiple fibers, or a bundle of fibers, could be used to collect light emerging from the droplet at multiple points.

Figure 23:
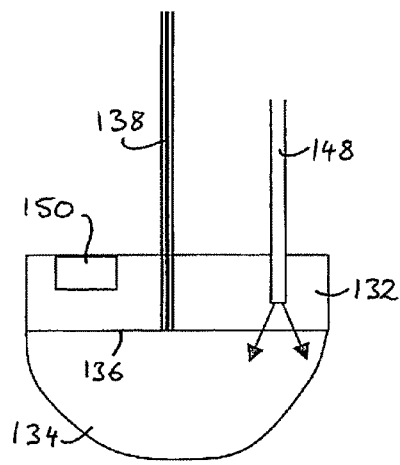
Figure 24:
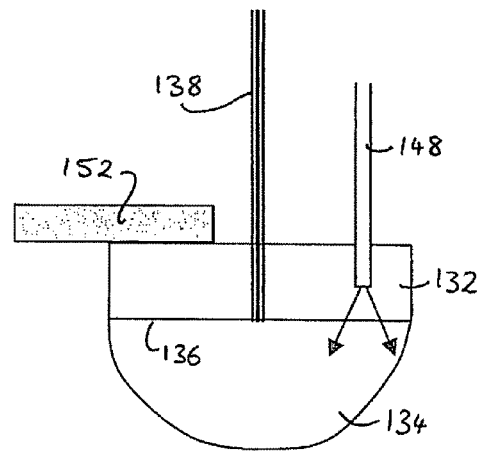

In FIG. 23, the source is a fiber 148 and the detector is a silicon detector 150. In FIG. 24 the silicon detector is replaced by a CCD or CMOS detector 152.

The embodiments of FIGS. 21-24 can be implemented by integrating various semiconductor devices and other devices in materials such as silicon or quartz. Key issues are the wavelength of the light being emitted and the transparency of the material into which the light-emitting device is being embedded to the wavelength being emitted. (Silicon, for example, is transparent to IR). In practice it is possible to etch cavities in materials such as quartz and silicon in which could be placed light emitting devices.

Some of the more important points to consider in relation to the embodiments thus far described are:

The drop produces an array of paths from source to collector. The fact is, however, that if the volume of the drop is the same each time then a modified Beer's law applies, as will be described mathematically below. The pathlength is the integral of all paths, which can be obtained from calibration with standard drops of known absorbance.

The drop focuses the light and so it improves the collection efficiency because of the total internal reflective coupling of the rays.

Fibers can be placed in the plinth and not just in platform. Both options have been described.

CCD/CMOS detectors can be used rather than single collector fibers, to give measurements at numerous locations in the base of the plinth and a picture of the transmission characteristics of the drop.

The device could be fabricated as a chip (CCD/CMOS/silicon detector) with a fabricated silicon dioxide plinth. The source of the photons could be a fiber or a LED/Laser integrated in the device.

A UV source can excite the drop externally and fluorescence spectrophotometry measurements can be carried out instead of or in addition to straightforward spectrophotometry.

The platform can be tilted to help analysis; drop shapes can be changed by pressure variations; sucking the liquid into the head with a pump; or indeed numerous other ways making the drop a dynamic component of the analysis. Magnetic or electric field disturbances can also be applied to the drop. Various types of analysis can be carried out on the microvolume drops, such as employing capacitance, ultrasonic or any other tensiograph methods to obtain additional information. The use of ultrasonic excitations might be useful in certain bioassays in which it was for example important to degas the sample and note the effect of the change of composition with respect to a dissolved gas on the mobility or activity of say a protein, enzyme of important bio-molecule.

Liquid can be brought to the drophead using microfluidic arrangements.

The shape of the drop can be varied by adding micro-drops of (say) surfactants to just produce a mono layer using a spray or syringe method.

The plinth can be specially shaped using perhaps a 'figure eight' geometry to narrow the waist of the drop at a given point and thus reduce the volume held on the drophead.

Gases and vapors can be introduced above the drop to change the shape of the drop as the surface tension is determined by both phases, namely the LUT and the surrounding environment.

Bubble options could be used. In such embodiments a surrounding liquid phase might be employed instead of a vapor or gas.

The drophead component can be made disposable, which is particularly important for medical fluids that may carry disease.

As indicated above, it has been found that the equation for the drop spectrometers is the elegant modification of the Beer Lambert law.

The Effective Path Length (hereafter EPL) can be defined as $$l_1 = \int l P(l) dl \quad [1]$$

Here P(l) is the probability that a ray path of length l occurs in the rays being coupled from the source to the collector fiber and quite obviously $$1 = \int P(l) dl \quad [2]$$

The variance in the path lengths in the drop which are not equal is defined as:—

$$\Delta l^2 = (l_2^2 - l_1^2) \quad [3]$$

where $l_2$ is the rms path length defined as $l_2^2 = \int l^2 P(l) dl$.

The Beer's law representation is well known and given by:—

$$A = \log_{10}(e) \alpha l c = 0.4343 \alpha l = \epsilon c l \quad [4]$$

The Beer-Lambert Law, states that A is linearly proportional to the path length. Here $\alpha$ is the absorption coefficient and s is the molar absorptivity measured in $L \cdot mol^{-1} \cdot cm^{-1}$.

It has been shown that for drop spectrometers we obtain an absorption measurement from the signal that is equivalent to that of the UV-visible spectrophotometer. If we have a sample and a blank liquid then we can measure the photodetector signal of a blank and the test solutions we can obtain an absorption measurement thus;

$$A_T = \log_{10} \frac{\langle V_0 \rangle}{\langle V_t \rangle} (0 < A_T) \quad [5]$$

$\langle V_0 \rangle$ is the average voltage of the blank measured in volts.
$\langle V_t \rangle$ is the average voltage of the sample measured in volts.

$$A_T = 0.4343 \alpha l_1 c - 0.21715 \alpha^2 c^2 \Delta l^2 \quad [6a]$$

Which can be given using more usually used molar absorptivity thus;

$$A_T = \epsilon c l_1 - \epsilon^2 c^2 \Delta l^2 / (2 * 0.4343) \quad [6b]$$
$$= \epsilon c l_1 - 1.15278 \epsilon^2 c^2 \Delta l^2$$

These results 6a and 6b are the same result but presented in two standard forms. These equations for drop spectroscopy are obviously of considerable analytical importance to drop spectroscopy and shows that, for small absorption, the optical absorbance falls below the linear Beer's Law by an amount proportional to the variance of the EPL in the LUT. Of course, if the measurement involves a single EPL only, $l_2 = l_1$, and the absorbance A has the usual linear dependence on $\alpha l_1$. It is perhaps worth commenting on this correction factor to Beer's law. Common sense would suggest that if drop shapes of the LUT were essentially unchanged because we are analysing very dilute concentrations of analyte, then this correction factor is in essence just a quantifiable function of the absorbance of the test liquid. This result predicts that each aliquot used in the calibration will have a different correction factor, but it is a defined quantity and should be a constant in such analysis.

It is possible that given the sample does have an absorption spectrum in which at some wavelength there is no measured absorption, then it has been shown to be possible to use measurements at two different wavelengths to get the test (absorbing wavelength) and reference (non-absorbing wavelength). This is in some applications a useful approach and will obviously halve the analysis time.

In other words, if we have two wavelengths, one being a measuring wavelength (i.e. one at which an absorbance occurs) and the other being one at which there is no absorption, then the second measurement can be used to replace the necessity of making a blank measurement. The double-beam UV-vis has a cuvette with a sample and another containing a blank. Here we are using the exact physically identical drop to produce a measurement of both these signals. We have done this in practice and shown this technique gives accurate and reproducible measurements of absorbance.

Figure 25:
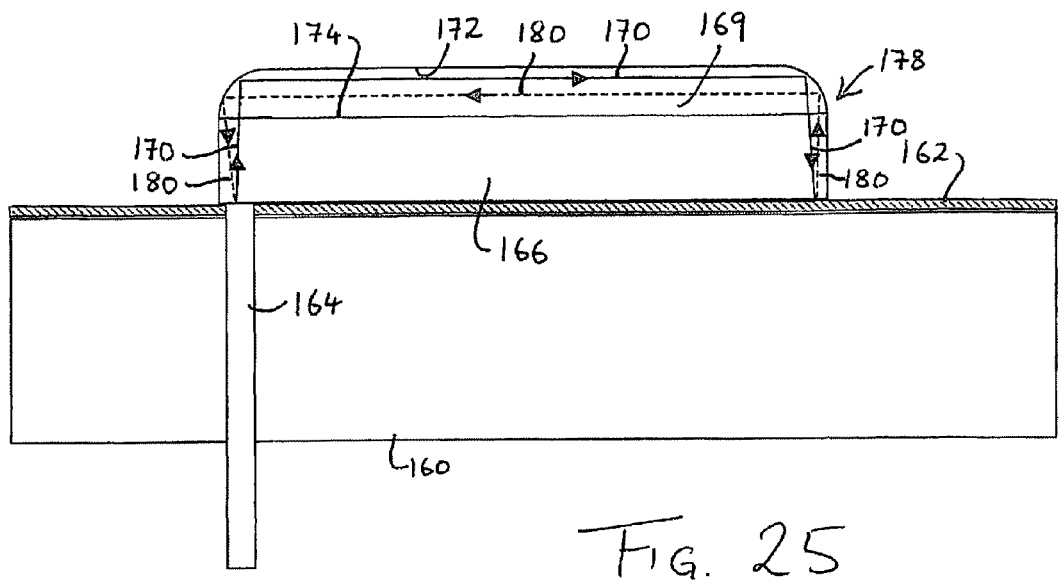

FIG. 25 shows a double-pass configuration of liquid drop analyzer. This is designed to maximise the pathlength of the light within the drop. The fabrication of focusing systems using microfabrication technologies could further enhance light coupling in these devices, incorporating not only mirrors but also gratings.

The FIG. 25 device has a platform 160 having an upper mirrored surface 162 through which the fiber 164 extends. A plinth 166 is mounted on the mirrored surface 162 and the fiber 164 terminates at this interface. Fiber 164 is a bifurcated (two-way) fiber used both to inject light into the drop 168 and to collect light emerging from the drop.

The plinth itself is of an elongated rectangular form so that a drop 169 placed on the plinth's surface takes up an elongated form as shown. Light entering the drop along the path indicated by the solid line 170 is reflected on the internal surface 172 of the drop and travels generally parallel to the drop-supporting surface 174. On emerging from the drop at the far end 178, the light reflects from mirrored surface 162 to travel on a similar but reversed return path as indicated by the broken line 180. The bifurcated fiber collects this reflected light which has undergone a double pass through the drop. Alternatively, two fibers could be used, one as source and the other as collector, along with the many other source/collector variations described previously.

The advantage in maximising wavelength can be understood theoretically in that Beer's law shows the measurement of absorption is an almost linear function of path length. Clearly the larger the path length the larger the absorption and this is the same in drops as in cuvettes. However, since these are microdrops, we are dealing with small path lengths (typically 1.1 mm for the drop sizes tested, as opposed to 10 mm in a cuvette) and the importance of maximising this becomes crucial with respect to the sensitivity of the measurement, which depends directly on this path length. The signal to noise of the instrument is also obviously a function of this path length.

Special deposition systems could be employed for liquid drop deposition on an elongated plinth, such as a nano-droplet spray. It is found however that in practice drops on rectangular plinth of 3 mm length and 1 mm width are quite simple to deposit with a micro-syringe.

Figure 26:
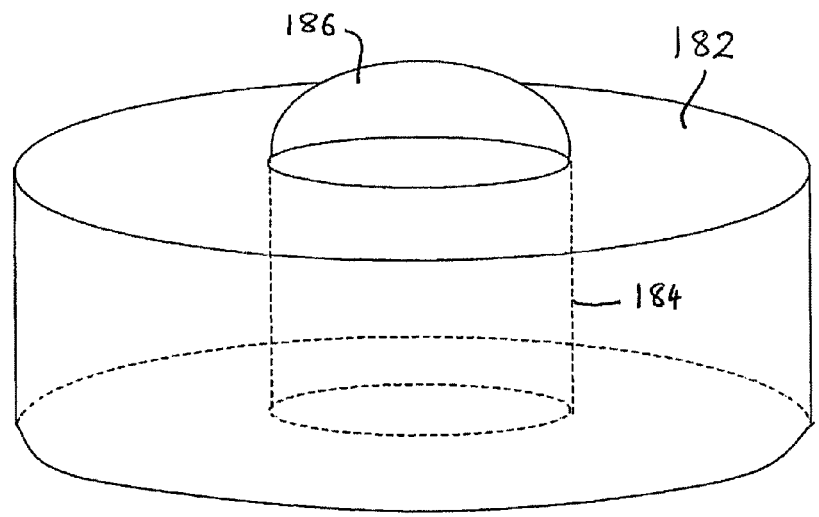
FIG. 26 is a perspective view of an alternative drophead.

FIG. 26 shows a drophead employing a repulsive annular ring 182 surrounding a central plinth 184 which is attractive to the liquid under test 186. Such an arrangement can resolve a problem that we have found of methanol not being retained on a quartz plinth. The repulsive material would depend here on what kind of LUT is used. If the liquid is hydrophilic such as we have in the materials supporting water, then we need a hydrophobic material surrounding such drops. For other liquids we may need the opposite type of plinth surface activities namely a hydrophobic plinth and hydrophilic surround.

To enable analysis of liquids having different properties the plinth can be manufactured using quartz, and a middle ring that is hydrophobic towards water. Depending on the properties of the LUT, the droplet could be repulsed by the border between the outer ring and the middle ring or the border between the inner ring and middle ring. In both cases the inner ring would be fabricated from UV transparent quartz. Because the surface of ring 182 might become damaged more easily than the durable quartz central plinth 184, these two components may be provided in an assembly which can be disassembled to replace ring 182 as necessary.

One can consider coating or treatment of surfaces to improve optical properties, such as for the reduction of Fresnel reflections. It is possible using microfabrication deposition techniques to put down individual films or combinations of film layers that display various optical properties such as Anti-Reflection Coatings (ARC) or to behave as Bragg Mirrors. It is necessary when using these films to match the depositions with comprehensive optical modelling in order to match the behaviour of the films to the wavelength of the radiation being used.

For instance there might be a need to change the properties of the surfaces involved for fluorescence. Fluorescence technologies offer a great diversity of technical designs from the use of lasers to excite emissions from very specific target molecules, to surface fluorescence, to excitation of marker molecules that are attached to enzymes and other molecules of interest. Blocking the fluorescence excitation, but allowing the passage of the fluorescence signal can be very useful and such coatings can be easily fabricated on plinths, substrates, fiber ends or indeed made as discrete components to use in conjunction with these optical heads. The coatings may be for the purpose of optical, adhesion, electrical focussing or indeed combinations of reasons.

These designs could be adapted to use with CCD using a plastic overlay with many plinths to take the liquids, or indeed with plinth platforms fabricated onto the CCD chip directly.

Figure 27:
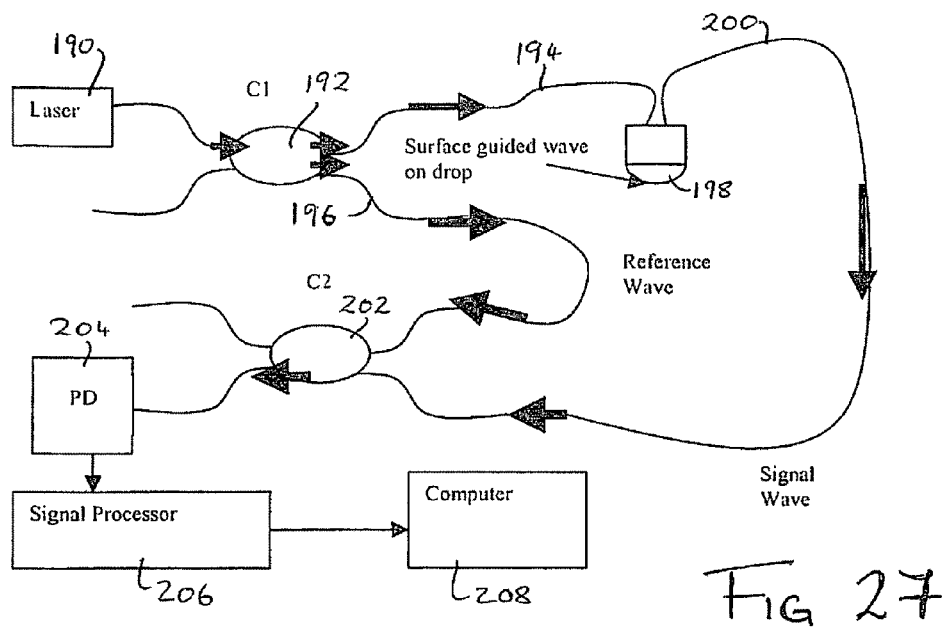
FIGS. 27 and 28 are illustrations of interferometer arrangements incorporating analysers.

FIG. 27 shows the use of an interferometry technique in conjunction with an analyser which is set up to allow surface guided waves (SGWs), such as is described above in relation to FIG. 18. A light ray which follows an SGW path will have a single pathlength around the drop. Interferometry will therefore allow the length of that path to be measured, or more accurately, will allow differences in that path length to be captured as an interference between the SGW light and a reference beam.

A laser source 190 sends light to a first coupler 192 which splits the light into a signal path 194 (equivalent to the source fiber in the FIG. 18 embodiment) and a reference path 196. The light from the signal path passes into a drophead and is coupled through a drop 198 as a surface guided wave before being collected by a detector fiber 200. The arrangement shown in FIG. 27 can be manufactured physically with monomode fibers, or can alternatively be fabricated on an IC with well-established and now very standard techniques. The arrangement of using two couplers is as stated above just one way to achieve this fiber interference geometry, and the skilled person will be able to achieve the same goal of coupling the SGW in the drop, thereby confining the wave to such a limited path on the perimeter of the drop that this enables an approximate phase coherence to be maintained in the transit of the wave in the drop.

It may be essential for interferometric measurements to have the drop suspended in a second phase with a saturated vapour environment to ensure there is no evaporation of the drop, thereby avoiding any changes in path length due to evaporation. A different approach might be taken in cases where interferometry was being used to measure the effects of evaporation or of droplet volume increases due to absorption from the surrounding second phase.

The form of this interference will of course depend on the phase relation in the two waves. The reference wave will have a constant phase at the photodiode detector, while the signal wave will have a phase that depends on the path-length of the SGW in the drop. Because spatial coherence has been maintained in the drop transit, interference between the two waves (signal and reference) can be seen and measured, and from this changes in the path length can be deduced. The diagram does not show such components as isolators, which would protect the laser from being disturbed by reflected power from the coupler. Also terminators on the fiber ends are not shown. As an alternative to a system made of discrete components such as couplers and monomode fibers, an equivalent optical arrangement could be fabricated on an IC with well-established and now very standard techniques.

One simple variation is the use of a mirror in the position of the collector fiber. In point of fact half of the drophead could be silvered, or indeed the entire drophead other than the area where the source fiber emits the source light into the drop as was described above in relation to FIG. 25. It would almost certainly be best practice here to place the silvered surface behind a thin quartz cylinder to stop the LUT from attacking and damaging the silvered surface.

Figure 28:
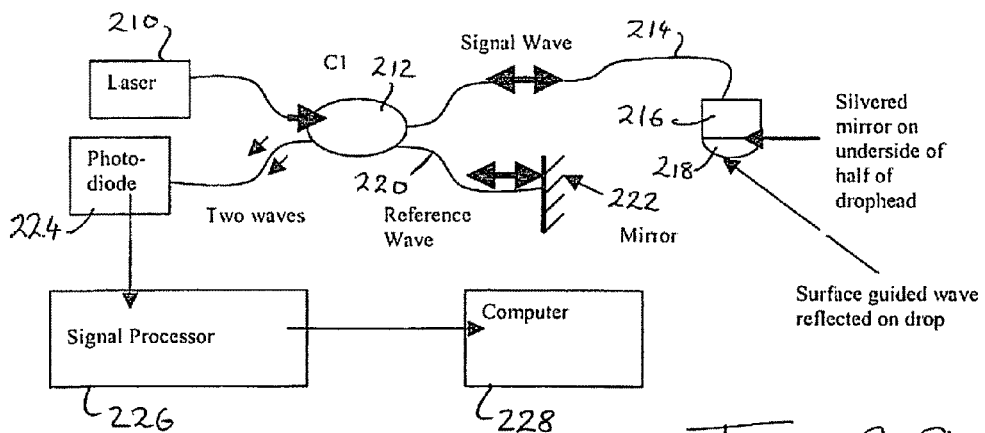

Such an interference geometry is shown in FIG. 28. This embodiment again has a laser 210, a coupler 212, and a signal path 214 feeding one of the coupler's output components to a drophead 216 having a silver mirror surface extending over half of the drophead. Light entering the drop 218 as an SGW from the signal fiber 214 reaches the opposite side of the drop-supporting surface whereupon it is reflected back and collected by the same signal fiber 214.

The other component of light from the coupler 212 is directed along a reference path 220 and reflected from a mirror 222 so that it too travels back along the same path to the coupler. Light travelling back along the signal path 214 from the drophead (following a double traverse of the surface of the drop) is combined with light travelling back along reference path 220 after reflection at mirror 222. The combined light signal is directed out of coupler 212 to photodiode 224 where an output signal is generated to a signal processor 226 and computer 228. Interference is once again exhibited and variations in the path length of the SGW in the drop can be measured. However, this embodiment also implicitly amplifies such changes in path length because of the double traversal of the drop, so that a variation x in the path length along the surface of the drop is seen as a variation 2x the path length of the light travelling along the surface to and from the mirrored surface of the drophead. This will consequently double the spatial sensitivity of the measurement.

The use of a Fiber Bragg Grating (FBG) in the reference arm in place of a mirror would allow the reflection of just one wavelength back to the photodetector (or more probably a CCD or CMOS detector system). Given that the pixels on the detector can then individually look at the situation vis-à-vis all wavelengths, it would be possible to measure interference perhaps at one detector wavelength. By using a broadband source, the FBG could be tunable to enable a specific wavelength to be brought up for interrogation and perhaps adjusted to a fluorescence emission of UV absorption. This geometry offers several possible experimental geometries and arrangements that might be devised for a specific application.

The dynamic situation in a drop could then be monitored to effect (i) the measurement of the arrival at the drop surface of surfactant molecules (These processes can take an appreciable time) to monitor shape changes in the drop (ii) the reaction of enzymes on the surface with proteins to change the shape of the drop (ii) the competition processes between a protein and a surfactant (iv) the evaporation of a component in the drop to change its volume (v) a chemical reaction process in the drop (iv) the reaction of a second phase component with the LUT in the drop, or indeed many, many other possible experimental proposals.

Figure 29:
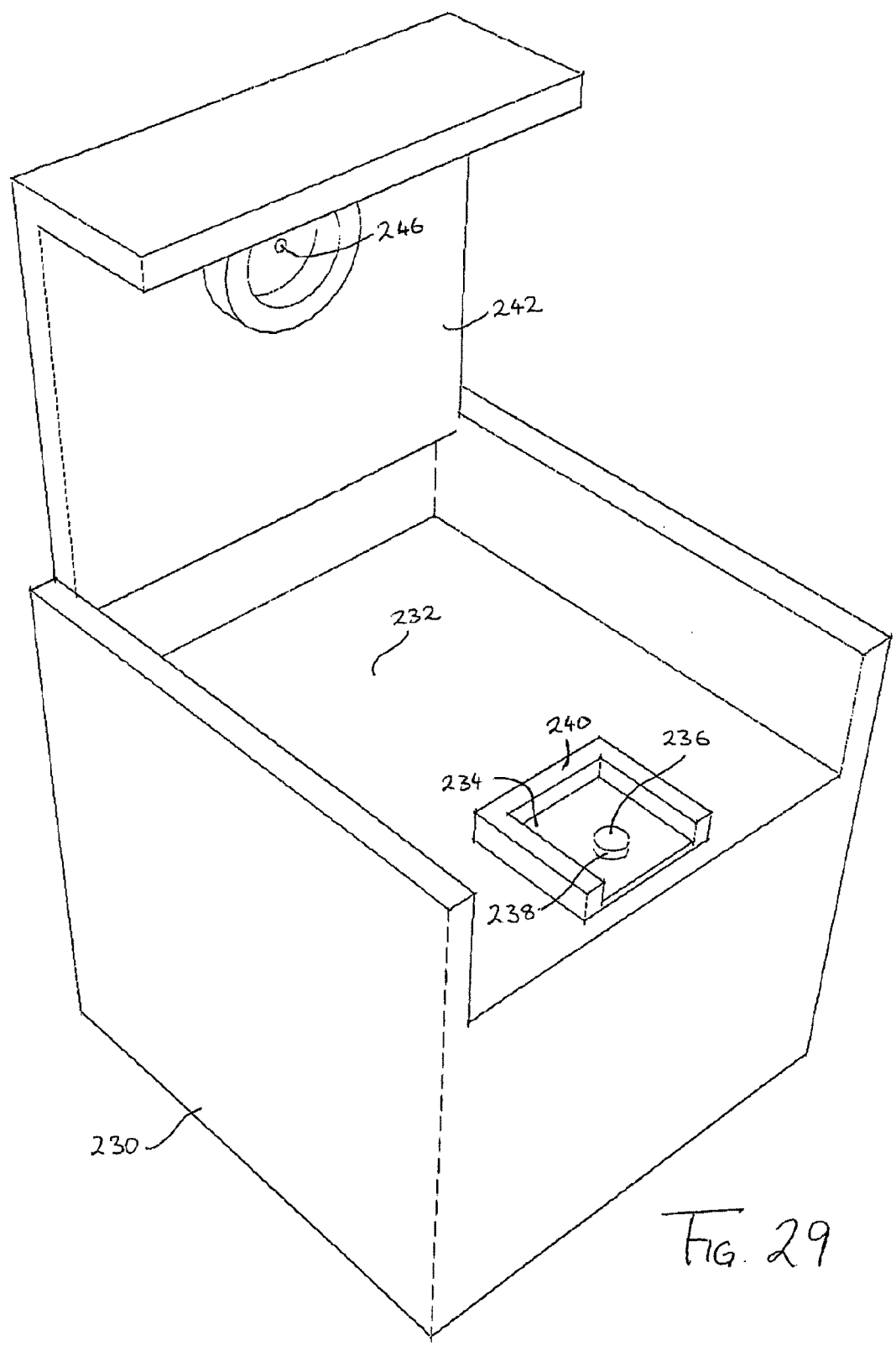
FIG. 29 is a perspective view of an instrument incorporating an analyser.

FIG. 29 shows one example of a working instrument in which a housing 230 has an upper surface 232 having a sample area 234 from which the drop-supporting surface 236 of a plinth 238 protrudes. A border 240 defines the sample area 234 to assist in cleaning of the sample area between measurements, and also acts as a light baffle to further shield the detector fiber from light sources other than that of the source.

A lid 242 can be raised and lowered to isolate the sample area from the external environment and to prevent unwanted illumination from reaching a drop (not shown) on drop-supporting surface 236. Mounted in the lid is a fiberoptic cable which terminates at a terminal end 246 for illumination of the drop when the lid is closed. A detector fiber (now shown) is mounted under the plinth for collecting light passing into the plinth via the drop as described above. The source fiber and the detector fiber may be plugged into an external source and an external detection system, or those elements can be built into the housing 230 as desired.

The device can be employed for UV measurements and for fluorescence measurements, with appropriate samples and using appropriate excitation frequencies.

Figure 32:
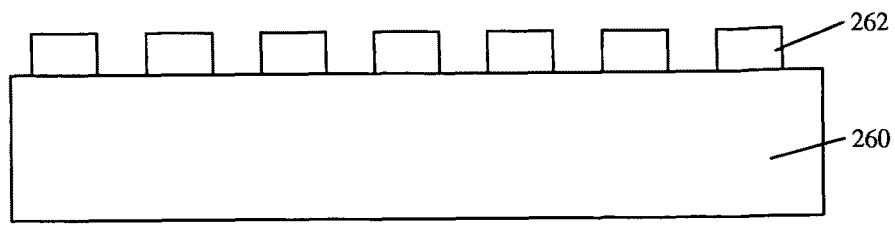
FIGS. 32 to 36 are schematic illustrations of fabrication methods for manufacturing dropheads using solid state fabrication techniques.

FIG. 32 illustrates a first fabrication technique for creating devices according to the invention, comprising a silicon wafer 260 having silicon dioxide plinths 262 etched thereon.

Figure 33:
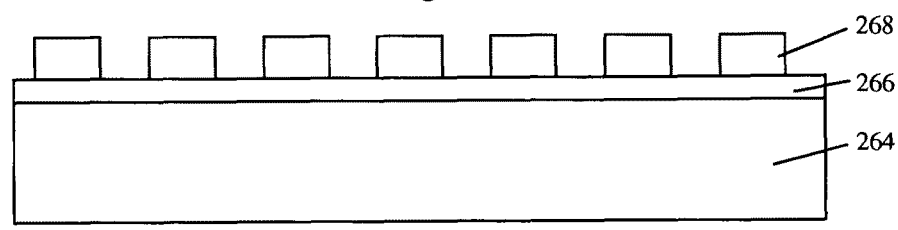

FIG. 33 shows a plurality of silicon plinths etched from a silicon-on-insulator (SOI) structure having a silicon bulk wafer 264, a buried silicon dioxide layer 266, and an outer silicon layer which is etched away to create the plinths 268.

Figure 34A:
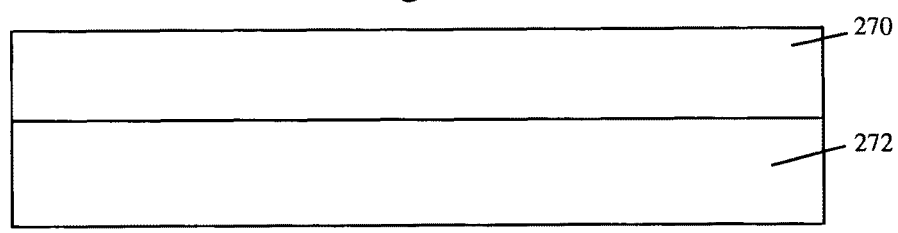
Figure 34B:
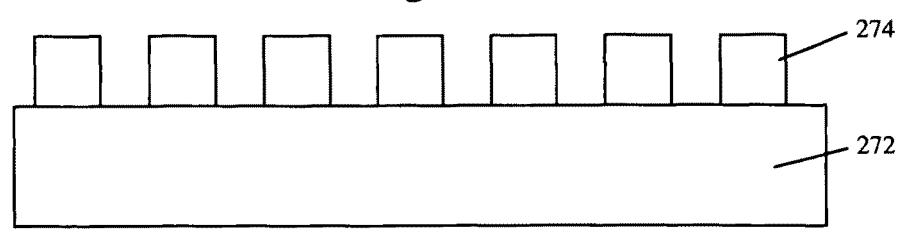

FIG. 34A shows a quartz wafer 270 bonded to a silicon wafer 272. In FIG. 34B the quartz wafer has been etched away to define a plurality of quartz plinths 274 sitting on a silicon substrate.

Figure 35:
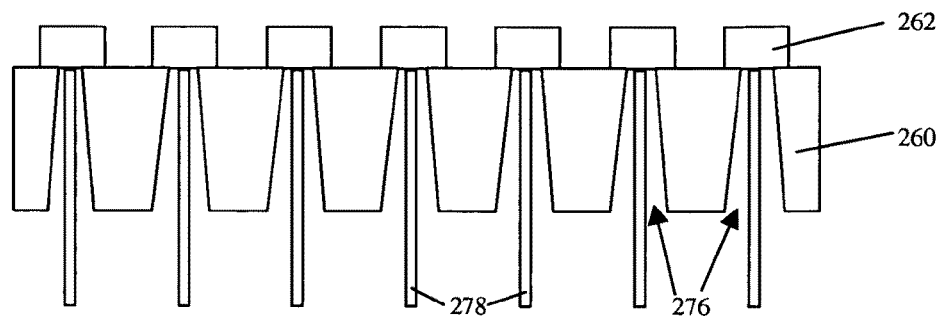

FIG. 35 shows a silicon wafer 260 with etched silicon dioxide plinths 262 (in accordance with FIG. 32), in which through-holes 276 have been etched to allow fibers 278 to be placed onto the underside of the quartz plinths 262.

Figure 36:
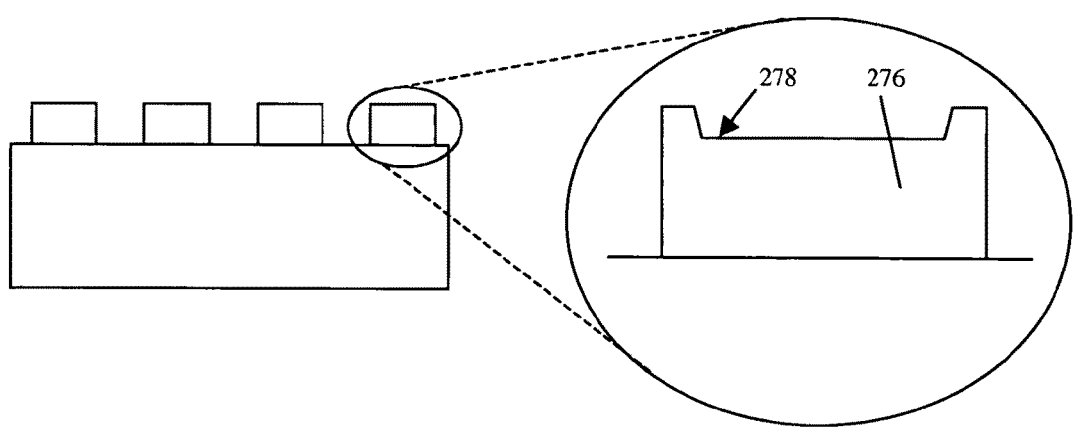

As illustrated in FIG. 36, a plinth 280 produced according to any of these microfabrication techniques can have the top surface 282 patterned with drop containment features or optical enhancement features.

The invention is not limited to the embodiment(s) described herein but can be amended or modified without departing from the scope of the present invention.

The invention claimed is:

1. An analyzer comprising:
a source of electromagnetic radiation, a detector for said radiation and a drophead in the form of a solid body which is transparent to said electromagnetic radiation, the drophead comprising a terminal surface which is adapted to receive a drop of liquid to be tested, wherein at least one of said source and said detector comprises an optical fiber for respectively transmitting or receiving said electromagnetic radiation to or from said received drop of liquid through said transparent drophead, the optical fiber terminating behind said terminal surface of said drophead the drophead being positioned in use relative to the source and detector to illuminate a drop received thereon and to cause an interaction in the path of the electromagnetic radiation between the source and detector, wherein said terminal surface of said drophead is dimensioned to constrain a drop which covers said terminal surface and is confined to said terminal surface to adopt a shape which is dominated more by surface tension forces than by gravitational forces.

2. An analyzer as claimed in claim 1, wherein said surface of said drophead is dimensioned to receive a maximum drop size of less than 10 microliters.

3. An analyzer as claimed in claim 2, wherein said surface of said drophead is dimensioned to receive a maximum drop size of 0.5 to 5 microliters.

4. An analyzer as claimed in claim 3, wherein said surface of said drophead is dimensioned to receive a maximum drop size in the range of 1 to 4 microliters.

5. An analyzer as claimed in claim 1, further comprising a mounting body on which said drophead is mounted.

6. An analyzer as claimed in claim 5, wherein said optical fiber is mounted in said mounting body and terminates at an interface between the mounting body and the drophead.

7. An analyzer as claimed in claim 5, comprising a plurality of said dropheads mounted on said mounting body.

8. An analyzer as claimed in claim 7, further comprising a plurality of said detectors, wherein each of said dropheads has one or more of said plurality of detectors associated therewith.

9. An analyzer as claimed in claim 8, wherein each of said dropheads has one or more of said plurality of detectors associated exclusively therewith.

10. An analyzer as claimed in claim 8, wherein said mounting body comprises a solid state detector array and said detectors are individual detection elements of said array positioned to receive electromagnetic radiation from said dropheads.

11. An analyzer as claimed in claim 10, wherein said solid state detector array is selected from a charge coupled detector array, and an array of diodes.

12. An analyzer as claimed in claim 8, wherein said mounting body comprises a plurality of optical fibers each mounted within said mounting body to receive electromagnetic radiation from a respective drophead.

13. An analyzer as claimed in claim 1, wherein said drophead comprises a plurality of drop-supporting surfaces isolated from one another by one or more structural features adapted to confine a drop to a single drop-supporting surface.

14. An analyzer as claimed in claim 13, wherein said one or more structural features comprise a surface region of different hydrophilicity than the plurality of drop-supporting surfaces, whereby said liquid drops are confined to the drop-supporting surface with which they have an affinity and are repelled from said surface region of different hydrophilicity.

15. An analyzer as claimed in claim 13, wherein said one or more structural features comprise surface discontinuities defining the plurality of drop-supporting surfaces, such that surface tension forces confine the drops to said drop-supporting regions bounded by said surface discontinuities.

16. An analyzer as claimed in claim 1, further comprising a microlens positioned below said drop-supporting surface for focusing radiation to or from said source and/or detector, respectively.

17. An analyzer as claimed in claim 1, further comprising one or more electrodes adjacent the drop-supporting surface which when suitably energized cause the physical shape or position of said received drop to alter, thereby enabling the characteristics of the drop to be measured in different shapes or positions.

18. An analyzer as claimed in claim 1, further comprising means for vibrating the drop.

19. An analyzer as claimed in claim 18, wherein said means for analyzing the drop comprises an oscillator coupled to a piezoelectric structure associated with the drop-supporting surface, whereby suitable energisation of the oscillator causes the piezoelectric structure to vibrate a drop supported on said surface.

20. An analyzer as claimed in claim 18, wherein said means for vibrating the drop comprises an ultrasonic generator for coupling ultrasound energy into the drop.

21. An analyzer as claimed in claim 1, further comprising a conduit for feeding a liquid to or from said drop-supporting surface to thereby allow the volume of a drop on said surface to be varied.

22. An analyzer as claimed in claim 1, further comprising deposition means for depositing a further liquid on the surface of a drop supported on said drop-supporting surface.

23. An analyzer as claimed in claim 22, wherein said deposition means is controllable to deposit an amount of further liquid calculated to produce a monolayer.

24. An analyzer as claimed in claim 1, wherein said source and said detector are positioned relative to the drop supporting surface to deliver said electromagnetic radiation to said drop along a path causing a portion of said radiation to travel as a surface guided wave along a part of its path between the source and the detector.

25. An analyzer as claimed in claim 24, wherein said path between said source and said detector, including said surface guided wave path, form part of an interferometer arrangement allowing variations in the length of said path to be calculated to within an order of magnitude of the wavelength of said radiation.

26. An analyzer as claimed in claim 1, wherein said drophead includes a reflective portion adapted to reflect radiation passing through the drop between the source and the detector whereby said radiation traverses the drop twice, first from said source to said reflective portion via said drop and then from said reflective portion to said detector via said drop.

27. An analyzer as claimed in claim 1, wherein said drop-supporting surface is formed in a well structure within a drophead.

28. An analyzer as claimed in claim 1, wherein said drop-supporting surface is elongated along one axis and wherein said source and said detector are positioned to direct light through said drop generally along said axis.

29. An analyzer as claimed in claim 1, further comprising a housing generally opaque to said electromagnetic radiation.

30. An analyzer as claimed in claim 29, wherein said housing is adapted to open to allow access to said drop-supporting surface and is adapted to close to shield said drop from external radiation during measurements.

31. An analyzer as claimed in claim 1, wherein said source is mounted above the drophead and is adapted to transmit said radiation as a wavefront approaching said drop-supporting surface at a non-zero angle.

\* \* \* \* \*